US007033812B2

(12) United States Patent
Zhong et al.

(10) Patent No.: US 7,033,812 B2
(45) Date of Patent: Apr. 25, 2006

(54) β-SECRETASE AND MODULATION OF β-SECRETASE ACTIVITY

(75) Inventors: Ziyang Zhong, Union City, CA (US); Barbara Cordell, Palo Alto, CA (US); Diana Hom Quon, Redwood City, CA (US); Yu-Wang Liu, Santa Clara, CA (US); Qiang Xu, Cupertino, CA (US); Frauke Schimmöller, Menlo Park, CA (US); Paul Andrew Hyslop, Indianapolis, IN (US); Edward Marion Johnstone, Indianapolis, IN (US); Sheila Parks Little, Indianapolis, IN (US); Steven Wyatt Queener, Indianapolis, IN (US); Tinggui Yin, Indianapolis, IN (US)

(73) Assignees: Scios Inc., Fremont, CA (US); Eli Lilly and Company, Indianapolis, IN (US)

( * ) Notice: Subject to any disclaimer, the term of this patent is extended or adjusted under 35 U.S.C. 154(b) by 17 days.

(21) Appl. No.: 10/740,865

(22) Filed: Dec. 18, 2003

(65) Prior Publication Data

US 2004/0132159 A1 Jul. 8, 2004

Related U.S. Application Data

(62) Division of application No. 09/566,746, filed on May 9, 2000, now abandoned.

(60) Provisional application No. 60/134,074, filed on May 13, 1999.

(51) Int. Cl.
*C12N 9/64* (2006.01)
*C12N 9/50* (2006.01)

(52) U.S. Cl. ...................................... 435/226; 435/219

(58) Field of Classification Search ............... 435/219, 435/226
See application file for complete search history.

(56) References Cited

U.S. PATENT DOCUMENTS

| | | | |
|---|---|---|---|
| 5,200,339 A | 4/1993 | Abraham | 435/212 |
| 5,292,652 A | 3/1994 | Dovey et al. | 435/226 |
| 5,424,205 A | 6/1995 | Dovey et al. | 435/226 |
| 5,744,346 A | 4/1998 | Chrysler et al. | 435/226 |
| 5,849,560 A | 12/1998 | Abraham | 435/219 |
| 5,942,400 A | 8/1999 | Anderson et al. | 435/7.1 |
| 6,162,630 A | 12/2000 | Powell et al. | 435/219 |

FOREIGN PATENT DOCUMENTS

| | | |
|---|---|---|
| EP | 0 85544 | 1/1998 |
| WO | WO 91/13905 | 9/1991 |
| WO | WO 92/07068 | 4/1992 |
| WO | WO 95/13084 | 5/1995 |

(Continued)

OTHER PUBLICATIONS

Abraham et al., *Biochem Biophys Res Comm* 174(2):790-796 (1991).

(Continued)

*Primary Examiner*—Rebecca E. Prouty
*Assistant Examiner*—Malgorzata A. Walicka
(74) *Attorney, Agent, or Firm*—Morrison & Foerster LLP

(57) ABSTRACT

The invention concerns a novel β-secretase, a method of partially purifying this novel β-secretase, and its use in assays to screen for potential drug candidates against Alzheimer's disease and other neurological diseases. The novel β-secretase has an estimated molecular weight of about 32–39 kDa or 22–26 kDa in HEK293 cell membrane extracts and human brain samples, respectively, as calculated from radiation inactivation analysis, and has a pH optimum at about pH 6.5–7.0.

2 Claims, 13 Drawing Sheets

ELISA Assay Overview

APP751sw/β-secretase complex

β-secretase cleavage

Solubilized, partially purified P2 membranes
Incubation o/n @ 37°C mAb 8E5
(antibody to coat plate )

192sw or equivalent ab (e.g. AF20)

β-NTFsw

Goat-anti-Rabbit IgG-HRP

TMB/ $H_2SO_4$

FOREIGN PATENT DOCUMENTS

| | | |
|---|---|---|
| WO | WO 96/31122 | 8/1996 |
| WO | WO 96/40885 | 12/1996 |
| WO | WO 00/58479 | 10/2000 |

OTHER PUBLICATIONS

Abraham et al., *J Lab Clin Med* 133(5):507-515 (1999).
Brown et al., *J Neurochem* 66(8):2436-45 (1996).
Cai et al., *Science* 259:514-516 (1993).
Checler, *J Neurochem* 65;1431-1444 (1995).
Chevalier et al., *Brain Res* 750:11-19 (1997).
Chevalier et al., *Brit J Pharm* 121:556-562 (1997).
Citron et al., *Neuron* 14:661-670 (1995).
Citron et al., *Neuron* 17:171-179 (1996).
Clark et al., *Arch Neurol* 50:1164-1172 (1993).
Dreyer et al., *FEBS 224:265-271* (1994).
Farzan et al., *PNAS USA* 97:9712-9717 (2000).
Games et al., *Nature* 373:523-525 (1995).
Glenner et al., *J Neurol Sci* 94:1-18 (1989).
Goodison et al., *J Neuropath Exper Neurol* 52:192-198 (1993).
Gouras et al., *PNAS* 97:1202-1205 (2000).
Greenberg et al., *Neurology* 43:2073-2079 (1993).
Grüninger-Leicht et al., *Nature Biotech* 18-66:70 (2000).
Haan et al., *Clin Neurol Neurosurg* 92(4):305-310 (1990).
Haan et al., *Dementia* 5:210-213 (1994).
Haass et al., *J Bio Chem* 268:3021-3025 (1993).
Hardy, *Nature Genetics* 1:233-234 (1992).
Hardy, *Alzheimer's Disease Update*, 10:239-247 (1994).
Hardy, *TINS* 20:154-159 (1997).
Higaki et al., *J Biol Chem* 371 (5):31885-31893 (1996).
Hsiao et al., *Science* 372:99-102 (1996).
Huber et al., *J Neurochem* 72(3):1215-1223 (1999).
Hussain et al., *Mol Cel Neurosci* 14:419-427 (1999).
Igarashi et al., *Biochem Biophys Res Comm* 185(3):1000-1004 (1992).
Ishiura et al., *FEBS Lett*. 257(2):388-92 (1989).
Ishiura et al., *Neurosci Lett* 115:329-334 (1990).
Itoh et al., *J Neurol Sci* 116:135-141 (1993).
Johnson-Wood et al., *PNAS USA* 94:1550-1555 (1997).
Kalaria et al., *NeuroReport* 6:477-480 (1995).
Kawai et al., *Brain Res* 623:142-146 (1993).
Kempner, E.S., *Analyt Biochem* 278:113-123 (1999).
Kempner, E.S., *TIBWS* 18:236-239 (1993).
Kiragucgi et al., *Nature* 331:530-532 (1988).
Knops et al., *J Biol Chem* 270:2419-2422 (1995).
Koike et al., *J Biochem* 126:235-242 (1999).
Kojima et al., *FEBS* 304(1):57-60 (1992).
Konno et al., *PNAS* 97:1456-1460 (2000).
Ladror et al., *J Biol Chem* 269(28):18422-18428 (1994).
Lannfelt et al., *Biochem Neuro Dis* 22:176-179.
LePage et al., *FEBS Letters* 377:367-370 (1995).
Leveugle et al., *Em Int* 30(6):543-588 (1997).
Levy et al., *Science* 248:1124-1126 (1990).
Little et al., *J Bio Chem* 272(10):25135-25142 (1997).
Maat-Schieman et al., *Acta Neuropath* 88:371-378 (1994).
Mandybur, *Acta Neuropath* 78:329-333 (1989).
Marks et al., *Peptides* 15(1):175-182 (1994).
Martin et al., *Am J Path* 145:1358-1381 (1994).
Masilah et al., *J Neurosci* 16(18):5795-5811 (1996).
Matsumoto et al., *Biochem* 33:3941-3948 (1994).
Matsumoto et al., *Neurosci Lett* 195:171-174 (1995).
Matsumoto, *Mole Neurosci* II(27)373-377 (2000).
McDermott et al., *Biochem Biophys Res Comm* 185(2):746-752 (1992).
McDermott et al., *Neurosci Res Comm* 8(3):185-190 (1991).
Moran et al., *PNAS USA* 92:5341-5345 (1995).
Nelson et al., *J Biolog Chem* 285(7):2836-3843 (1990).
Nelson et al., *J Neurochem* 61(2):567-5677 (1993).
Oyama et al., *J Neurochem* 62:1062-1066 (1994).
Papastoitsis et al., *Biochem* 33:192 (1994).
Pike et al., *J Neurochem* 64:253-265 (1995).
Ponte et al., *Nature* 331:525-527 (1998).
Razzaboni et al., *Brain Res* 589:207-216 (1992).
Razzaboni et al., *Neurobio Aging* 14:677-679 (1993).
Sahasrabudhet et al., *J Bio Chem* 268(22):16699-16705 (1993).
Sauder et al., *JMB* 300:241-248 (2000).
Schonlein et al., *Biochem Biophys Res Comm* 201(1):45-51 (1994).
Selkoe et al., *PNAS USA* 85:7341-7345 (1998).
Selkoe, *J Bio Chem* 271:18295-18298 (1996).
Selkoe, *Nature* 399:A23-A31 (1999).
Selkoe, *TINS* 16:403-409 (1993).
Seubert et al., *Nature* 361:260-263 (1993).
Siman et al., *J Neurosci* 10(7):2400-2411 (1990).
Sinha et al., *Nature* 402:537-540 (1999).
Tanzi et al., *Nature* 331:529-530 (1988).
Thompson et al., *Biochem Biophys Res Comm* 213:66-73 (1995).
Tsukada et al., *Brain Res* 750:11-19 (1997).
Vassar et al., *Science* 286:735-41 (1999).
Vinters, *Stroke* 18:311-324 (1987).
Wattendorf, *J Neurol, Neurosurg, Psych* 58:699-705 (1995).
Wisniewski et al., *Ann Neurol* 17:278-282 (1985).
Wolfe, *J Med Chem* 44:2039-2060 (2001).
Yamada et al., *J Neurol, Neurosurg, Psych* 56:543-547 (1993).
Yan et al., *Nature* 402:533-537 (1999).

β-SECRETASE AND MODULATION OF β-SECRETASE ACTIVITY

This application is a divisional of U.S. patent application Ser. No. 09/556,746 filed on May 9, 2000, now abandoned, which claims benefit of priority to U.S. provisional application Ser. No. 60/134,074 filed on May 13, 1999. The disclosures of each of these applications are hereby incorporated by reference in their entireties.

BACKGROUND OF THE INVENTION

1. Field of the Invention

The present invention concerns a novel β-secretase, a method of partially purifying this novel β-secretase, and its use in assays to screen for potential drug candidates against Alzheimer's disease and other neurological diseases.

2. Description of the Related Art

A number of important neurological diseases, including Alzheimer's disease (AD), cerebral amyloid angiopathy (CAA), and prion-mediated diseases are characterized by the deposition of aggregated proteins, referred to amyloid, in the central nervous system (CNS) (for reviews, see Glenner et al., *J. Neurol. Sci.* 94:1–28 [1989]; Haan et al, *Clin. Neurol. Neurosurg.* 92(4):305–310 [1990]). These highly insoluble aggregates are composed of nonbranching, fibrillar proteins with the common characteristic of β-pleated sheet conformation. In the CNS, amyloid can be present in cerebral and meningeal blood vessels (cerebrovascular deposits) and in the brain parenchyma (plaques). Neuropathological studies in human and animal models indicate that cells proximal to amyloid deposits are disturbed in their normal functions (Mandybur, *Acta Neuropathol.* 78:329–331 [1989]; Kawai et al., *Brain Res.* 623:142–146 [1993]; Martin et al., *Am. J. Pathol.* 145:1348–1381 [1994]; Kalaria et al., *Nuroreport* 6:477–480 [1995]; Masliah et al., *J. Neurosci.* 16:5795–5811 [1996]; Selkoe, *J. Biol. Chem.* 271: 18295–18298 [1996]; Hardy, *Trends Neurosci* 20:154–159 [1997]).

AD and CAA share biochemical and neuropathological markers, but differ somewhat in the extent and location of amyloid deposits as well as in the symptoms exhibited by affected individuals. The neurodegenerative process of AD, the most common neurodegenerative disorder worldwide, is characterized by the progressive and irreversible deafferentation of the limbic system, association neocortex, and basal forebrain accompanied by neuritic plaque and tangle formation (for a review, see Terry et al., "Structural alteration in Alzheimer's disease," In: Alzheimer's disease, Terry et al. Eds., 1994, pp. 179–196, Raven Press, New York). Dystrophic neurites, as well as reactive astocytes and microglia, are associated with these amyloid-associated neuritic plaques. Although the neuritic population in any given plaques is mixed, the plaques generally are composed of spherical neurites that contain synaptic proteins, APP (type I), and fusiform neurites containing cytoskeletal proteins and paired helical filaments (PHF; type II).

CAA patients display various vascular syndromes, of which the most documented is cerebral parenchymal hemorrhage. Cerebral parenchymal hemorrhage is the result of extensive amyloid deposition within cerebral vessels (Hardy, *Trends Neurosci* 20:154–159 [1997]; Haan et al., *Clin. Neurol. Neurosurg.* 92:305–310 [1990]; Terry et al., supra; Vinters, *Stroke* 18:211–224 [1987]; Itoh et al., *J. Neurosurgical Sci.* 116:135–141 [1993]; Yamada et al., *J. Neurol. Neruosurg. Psychiatry* 56:543–547 [1993]; Greenberg et al., *Neurology* 43:2073–2079 [1993]; Levy et al., *Science* 248:1124–1126 [1990]). In some familial CAA cases, dementia was noted before the onset of hemorrhages, suggesting the possibility that cerebrovascular amyloid deposits may also interfere with cognitive functions.

Both AD and CAA are characterized by the accumulation of senile plaques in the brains of the affected individuals. The main amyloid components is the amyloid β protein (Aβ), also referred to as amyloid β or β-amyloid peptide, derived from proteolytic processing of the β-amyloid precursor protein, β-APP or simply APP. For review in connection with AD see, Selkoe, D. J. *Nature* 399: A23–A31 (1999). Aβ is produced by proteolytic cleavage of an integral membrane protein, termed the β-amyloid precursor protein (βAPP).

The Aβ peptide, which is generated from APP by two putative secretases, is present at low levels in the normal CNS and blood. Two major variants, $A\beta_{1-40}$ and $A\beta_{1-42}$ are produced by alternative carboxy-terminal truncation of APP (Selkoe et al. (1988) *Proc. Natl. Acad. Sci. USA* 85:7341–7345; Selkoe (1993) *Trends Neurosci* 16:403–409). $A\beta_{1-42}$ is the more fibrillogenic and more abundant of the two peptides in amyloid deposits of both AD and CAA. In addition to the amyloid deposits in AD cases described above, most AD cases are also associated with amyloid deposition in the vascular walls (Hardy (1997), supra; Haan et al. (1990), supra; Terry et al., supra; Vinters (1987), supra; Itoh, et al. (1993), supra; Yamada et al. (1993); supra; Greenberg et al. (1993), supra; Levy et al. (1990), supra). These vascular lesions are the hallmark of CAA, which can exist in the absence of AD.

The precise mechanisms by which neuritic plaques are formed and the relationship of plaque formation to the AD-associated, and CAA-associated neurodegenerative processes are not well-defined. However, evidence indicates that dysregulated expression and/or processing of APP gene products or derivatives of these gene products are involved in the pathophysiological process leading to neurodegeneration and plaque formation. For example, missense mutations in APP are tightly linked to autosomal dominant forms of AD (Hardy (1994) *Clin. Geriatr. Med.* 10:239–247; Mann et al. (1992) *Neurodegeneration* 1:201–215). The role of APP in neurodegenerative diseases is further implicated by the observation that persons with Down's syndrome who carry an additional copy of the human APP (hAPP) gene on their third chromosome 21 show an overexpression of hAPP (Goodison et al. (1993) *J. Neuropathol. Exp. Neurol.* 52:192–198; Oyama, et al. (1994) *J. Neurochem.* 62:1062–1066) as well as a prominent tendency to develop AD-type pathology early in life (Wisniewski et al. (1985) *Ann. Neurol.* 17:278–282). Mutations in Aβ are linked to CAA associated with hereditary cerebral hemorrhage with amyloidosis (Dutch HCHWA) (Levy, et al. (1990), supra), in which amyloid deposits preferentially occur in the cerebrovascular wall with some occurrence of diffuse plaques (Maat-Schieman et al. (1994) *Acta Neuropathol.* 88:371–8; Wartendorff et al. (1995) *J. Neurol. Neurosurg. Psychiatry* 58:699–705). A number of hAPP point mutations that are tightly associated with the development of familial AD encode amino acid changes close to either side of the Aβ peptide (for a review, see, e.g., Lannfelt et al. (1994) *Biochem. Soc. Trans.* 22:176–179; Clark et al. (1993) *Arch. Neurol.* 50:1164–1172). Finally, in vitro studies indicate that aggregated Aβ can induce neurodegeneration (see, e.g., Pike et al. (1995) *J. Neurochem.* 64:253–265).

APP is a glycosylated, single-membrane-spanning protein expressed in a wide variety of cells in many mammalian tissues. Examples of specific isotypes of APP which are currently known, to exist in humans are the 695-amino acid polypeptide described by Kang et al. (1987) *Nature* 325: 733–736, which is designated as the "normal" APP. A 751-amino acid polypeptide has been described by Ponte et al. (1988) *Nature* 331:525–527 and Tanzi et al. (1988) *Nature* 331:528–530. A 770-amino acid isotype of APP is described in Kitaguchi et al. (1988) *Nature* 331:530–532. A number of specific variants of APP have also been described having mutations which can differ in both position and phenotype. A general review of such mutations is pivoted in Hardy (1992) *Nature Genet.* 1:233–235. A mutation of particular interest is designated the "Swedish" mutation where the normal Lys-Met residues at positions 595 and 596 are replaced by Asn-Leu. This mutation is located directly upstream of the normal β-secretase cleavage site of APP, which occurs between residues 596 and 597 of the 695 isotype.

APP is post-translationally processed by several proteolytic pathways resulting in the secretion of various fragments or intracellular fragmentation and degradation. F. Checler, *J. Neurochem.* 65:1431–1444 (1995). The combined activity of β-secretase and γ-secretase on APP releases an intact β-amyloid peptide (Aβ), which is a major constituent of amyloid plaques. Aβ is an approximately 43 amino acid peptide which comprises residues 597–640 of the 695 amino acid isotype of APP. Internal cleavage of Aβ by a α-secretase inhibits the release of the full-length Aβ peptide. Although the extent of pathogenic involvement of the secretases in AD progression is not fully elucidated, these proteolytic events are known to either promote or inhibit Aβ formation, and thus are thought to be good therapeutic candidates for AD.

There are at least two proteases involved in the generation of Aβ, referred to as α- and γ-secretases (Citron et al., *Neuron* 17:171–179 [1996]; Seubert et al., *Nature* 361: 260–263 [1993]; Cai et al., *Science* 259:514–516 [1993]; and Citron et al., *Neuron* 14:661–670 [1995]). There have been intense efforts in recent years to identify and characterize these enzymes. Recently five independent groups have reported cloning and characterization of genes corresponding to β-secretase (Vassar et al., *Science* 286: 735–741 [1999]; Yan et al., *Nature* 402: 533–537 [1999]; Sinha et al., *Nature* 402: 537–540 [1999]; Hussain et al., *Mol. Cell. Neurosci.* 14: 419–427 [1999]; Lin et al. *Proc. Natl. Acad. Sci. USA* 97: 1456–1460 [2000]). The enzyme has been variously referred to as β-site APP-cleaving enzyme (BACE), Aspartyl protease-2 (Asp2), memapsin 2 or simply as β-secretase. However, the deduced amino acid sequence of the polypeptide chain reported by all four groups is identical. The cloned enzyme possesses many of the characteristics expected of an authentic β-secretase, such as the presence of conserved aspartyl protease active site motif (D[S/T]G), a signal peptide, a transmembrane domain, ability to act upon βAPP, enhanced cleavage of the Swedish mutant of βAPP, and intracellular localization in Golgi, endoplasmic reticulum, endosome/lysosome compartments. Thus, it appears that the newly identified enzyme represents an authentic β-secretase. However, none of these reports rule out the possibility of additional enzymes having β-secretase activities. There have been speculations about the possible involvement of more than one enzyme entity in β-cleavage of APP (e.g., Papastoitsis et al. *Biochem.* 33: 192–199 [1994]; Koike et al. *J. Biochem.* 126: 235–242 [1999]; Brown et al. *J. Neurochem.* 66: 2436–2445 [1996]; Chevallier et al. *Brain Res.* 750: 11–19 [1997]). Experiments with intact cells suggested that β-secretase has an acidic pH optimum (Haass et al., *J. Biol. Chem.* 268: 3021 [1993]; Knops et al., *J. Biol. Chem.* 270: 2419 [1995]). Indeed, the newly isolated and characterized β-secretase was found to have a pH optimum at 4.5 (Vassar et al., *Science* 286: 735–741 [1999]) or 5.0 (Sinha et al., *Nature* 402: 537–540 [1999]) for its activity. These characteristics are thought to be consistent with β-secretase activity in the endosomes/lysosomes where the pH is low. However, β-secretase is also known to function in the endoplasmic reticulum where the pH is neutral (around 7.0), an environment not well suited for an enzyme having an acidic pH optimum. It is, therefore, possible that there are more than one β-secretase enzymes involved in the proteolytic cleavage of β-APP.

The identification, isolation, purification, and characterization of all participants in the enzymatic cleavage of β-APP would permit chemical modeling of a critical event in the pathology of Alzheimer's disease and would allow the screening of compounds to determine their ability to inhibit in vivo β-secretase activity. For these reasons, it would be desirable to isolate, clone and characterize a β-secretase enzyme having a neutral pH preference. It would be also desirable to develop a method for the functional cloning of the genes encoding proteins or enzymes involved in the proteolytic cleavage of β-APP. It would further be desirable to identify inhibitors of the β-APP processing leading to Aβ release, and in particular to identify molecules that preferentially inhibit the β-secretase activity having a neutral (pH 6.5–7.0) pH optimum, or the β-secretase activity having an acidic (around pH 4.5) pH optimum.

SUMMARY OF THE INVENTION

The present invention is based on the recognition that more than one distinct enzymatic activities, substantially differing in their physicochemical and biological properties, may be involved in β-cleavage of APP, a critical event in the generation of the AP peptide. Of particular significance is a distinct difference in pH optima of these β-secretase activities. While a recently reported β-secretase enzyme is optimally active at acidic pH (pH 4.5–5.5), the novel β-secretase enzyme identified herein has a neutral (pH 6.5–7.0) pH optimum.

In one aspect, the present invention provides a method of identifying a compound characterized by an ability to alter β-secretase activity. The method comprises the steps of contacting a β-secretase enzyme having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples, with a candidate compound; and monitoring the effect of the candidate compound on the activity of the β-secretase enzyme.

In a specific embodiment, the β-secretase enzyme is contacted with the candidate compound in the presence of a β-amyloid precursor protein (APP). APP preferably is the human 695-amino acid isotype, and may contain the so called "Swedish" mutation, located directly upstream of the normal β-secretase cleavage site of APP. The α-secretase enzyme used in the assay may be in isolated, immobilized or cell bound form, and the assay is preferably is performed with a plurality of candidate compounds.

In a particular embodiment, the ability of a candidate compound to alter β-secretase activity is monitored by determining the amount of an APP proteolytic product, such as βNTF.

In another specific embodiment, the β-secretase enzyme having a quasi-neutral pH preference is contacted with the candidate compound(s) in the additional presence of a further β-secretase enzyme having a pH optimum at about pH 4.5–5.0 and an estimated molecular weight of about 50–60 kDa as calculated from radiation inactivation analysis of HEK293 cell membrane extracts or human brain samples.

The assay is preferably used to identify inhibitors of β-secretase activity. A preferred group of such inhibitors preferentially inhibits the activity of the β-secretase enzyme having a pH optimum at about pH 6.5–7.0.

In another aspect, the invention concerns a method for identifying a compound characterized by an ability to alter APP/β-secretase activity. The method comprises the steps of: contacting an APP/β-secretase mixture, isolated from membranes obtained from cells expressing APP and a β-secretase, with a candidate compound; and monitoring the effect of the candidate compound on β-secretase activity, wherein the APP/β-secretase mixture comprises a β-secretase enzyme having a pH optimum at about pH 6.5–7.0. In a preferred embodiment, the β-secretase enzyme has an estimated molecular weight of about 32–39 kDa or 20–26 kDa in HEK293 cell membrane extract and human brain samples, respectively, as calculated from radiation inactivation analysis. The method may be performed in the additional presence of a second β-secretase enzyme having a pH optimum at about 4.5–5, and an estimated molecular weight of about 50–60 kDa as calculated from radiation inactivation analysis of HEK293 cell membrane extracts or human brain samples. Also provided are inhibitors of β-secretase enzyme activity, identified by the aforementioned method, which, in a preferred embodiment, preferentially inhibit the activity of the first or the second β-secretase enzyme.

In a particular embodiment, the method involves monitoring the effect of a test compound on β-secretase activity by determining levels of APP proteolytic products, particularly after removing the background levels of APP proteolytic products. The levels of APP proteolytic products can, for example, be determined using an antibody that recognizes a β-secretase-produced APP proteolytic product. Thus, an antibody that selectively recognizes β-NTF, such as pAb AF-20, may be used for the purpose. In a variant of this method, the APP/β-secretase mixture is exposed, before addition of the test compound, to an agent that alters β-secretase activity or stabilizes the detectable β-secretase produced APP proteolytic products. In a preferred embodiment, the agent enhances the level of β-secretase activity. Suitable agents include phospholipids, such as cardiolipin, L-α-phosphatidylserine or L-α-phosphatidylinositol.

In yet another aspect, the present invention provides a method of identifying a compound characterized by the ability to alter APP β-secretase activity. The method comprises the steps of: providing membranes from cells expressing APP and a secretase; removing background levels of APP β-secretase proteolytic products from the membranes; isolating APP/β-secretase mixtures from the membranes; contacting the APP/β-secretase mixtures with a test compound; and determining levels of APP β-secretase proteolytic products; wherein the APP/β-secretase mixture comprises a β-secretase enzyme having a pH optimum at about pH 6.5–7.0, and the level of APP proteolytic products is indicative of the effect of the compound on in vivo β-secretase activity. Inhibitors of β-secretase enzyme activity identified by the method are also within the scope of the invention. In a preferred embodiment, the β-secretase enzyme has an estimated molecular weight of about 32–39 kDa or 20–26 kDa in HEK293 cell membrane extract and human brain samples, respectively, as calculated from radiation inactivation analysis. Optionally, the method is performed in the presence of a second β-secretase enzyme having a pH optimum at about 4.5–5.0. In a preferred embodiment, the second β-secretase enzyme has an estimated molecular weight of about 50–60 kDa as calculated from radiation inactivation analysis of HEK293 cell membrane extracts or human brain samples. Also provided are inhibitors of β-secretase enzyme activity, identified by the aforementioned method, which in a preferred embodiment, preferentially inhibit the activity of the first or the second α-secretase enzyme.

The effect of the candidate compound may be determined, for example, relative to a control APP/β-secretase mixture which is not in contact with the compound. In a specific embodiment, the APP/β-secretase mixture is pretreated so as to alter, particularly to enhance, β-secretase activity. A phospholipid such as cardiolipin, L-α-phosphatidylserine or L-α-phosphatidylinositol may, for example, be used for this purpose.

In a different aspect, the present invention provides a method for reducing α-amyloid plaque formation in a subject, comprising administering a compound determined to inhibit β-secretase activity by a method of the invention, in an amount sufficient to reduce in vivo APP β-secretase activity. Inhibition may result in decreased levels of N-terminal proteolysis of APP which is reflected in reduced release of β-amyloid peptide in brain tissue. In a preferred embodiment, the level of β-secretase activity is reduced to 30–80% below normal, and/or the level of β-amyloid release is reduced to 20–80% of normal. The compound may preferentially inhibit the activity of a β-secretase enzyme having a pH optimum at about pH 6.5–7.0 or a β-secretase enzyme having a pH optimum at about pH 4.5–5.0. In a preferred embodiment, the subject is a mammal, preferably a human particularly suffering from or predisposed to or prone to neurodegenerative disorders such as Alzheimer's disease or cerebral amyloid angiopathy.

In a still further aspect, the present invention concerns an isolated β-secretase enzyme having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples.

In another aspect, the invention concerns an APP/β-secretase mixture comprising a β-secretase enzyme having a pH optimum at about pH 6.5–7.0, and an estimated molecular weight of about 32–39 kDa or 20–26 kDa as calculated from radiation inactivation analysis of HEK293 cell membrane extracts and human brain samples, respectively. The mixture may further comprise a β-secretase enzyme having a pH optimum at about pH 4.5–5.0 and an estimated molecular weight of about 50–60 kDa as calculated from radiation inactivation analysis of HEK293 cell membrane extracts or human brain samples.

BRIEF DESCRIPTION OF THE DRAWINGS

FIG. 4 illustrates the effect of cardiolipin and the inhibition of β-secretase activity by the serine protease inhibitor, AEBSF (Pefabloc). FIG. 4A shows the differences in measured β-secretase activity, while

DETAILED DESCRIPTION OF PREFERRED EMBODIMENTS

Figure 1:
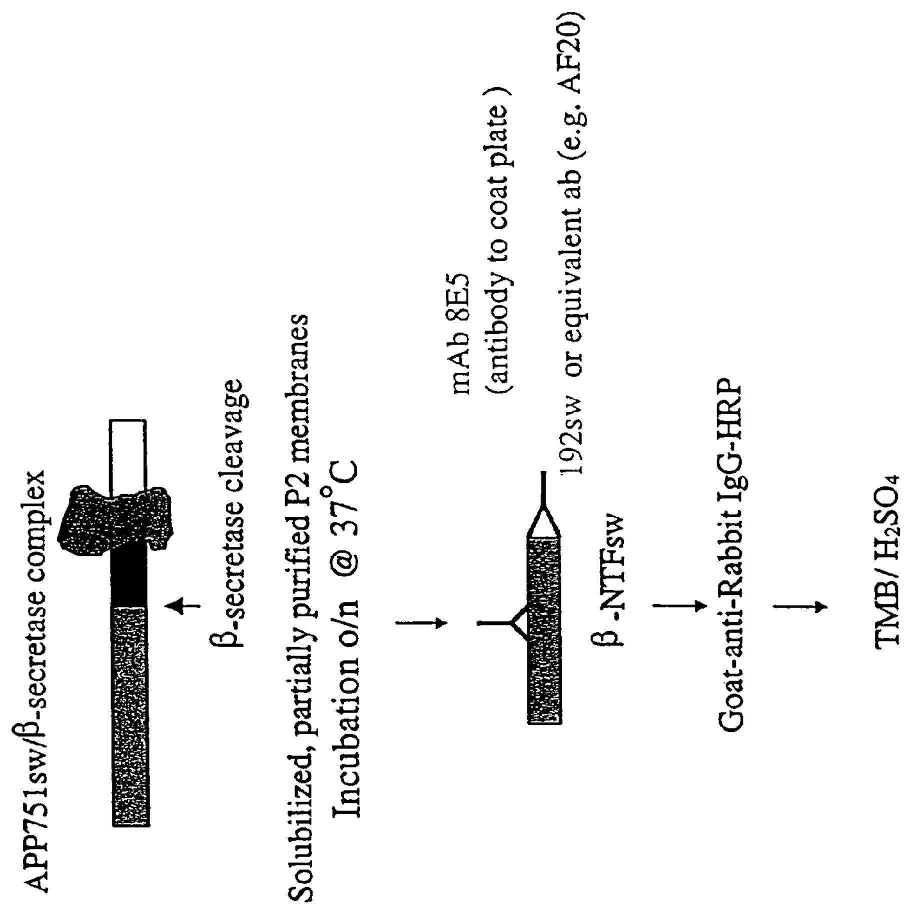
FIG. 1 is a schematic diagram illustrating the method of detecting α-secretase activity using an ELISA.

The present invention discloses a novel enymatic activity that prefers a quasi-neutral (pH 6.5–7.0) environment for proteolysis of βAPP substrate. This activity will be shortly referred to as "neutral" or "pH 6.5" β-secretase activity. The present invention further discloses a method of partial purification of this novel β-secretase activity, and its separation from the earlier reported β-secretase activity that is optimally active at acidic pH (pH 4.5–5.5), also referred to as "acidic" or "pH 4.5" activity.

The invention also discloses various ways of distinguishing between the two activities. For example, insensitivity of the neutral β-secretase activity to StatVal inhibitor sets it apart from the acidic pH-dependent β-secretase that is inhibited by this compound. The data disclosed herein also show that addition of the purified recombinant BACE only stimulates "pH 4.5" activity with no effect on "pH 6.5" activity. Conversely, the addition of partially purified novel neutral ("pH 6.5") activity only stimulates "pH 6.5" activity but not "pH 4.5" activity.

Finally, the data presented herein show that the estimated primary molecular mass of the protein responsible for the neutral β-secretase activity in human 293 cells is approximately 35.3 kDa as determined by the irradiation inactivation approach. This is significantly different from the predicted primary (i.e. devoid of secondary post-translational modifications) molecular weight of 51 kDa as reported for mature recombinant BACE (Vassar et al., *Science* 286: 735–741 [1999]). It is also different from the mass of approximately 57.9 kDa as estimated for endogenous BACE using the same irradiation inactivation method. Similarly, a significant difference in the estimated molecular mass was observed, using the same experimental approach, between β-secretase activities differing in their pH optima in human brain derived samples. Thus the present invention discloses a distinct novel β-secretase activity.

The assays of the present invention pave a way for screening of modulators, preferably inhibitors, of β-secretase activity and for the identification of potential drugs for Alzheimer's disease. Multiple β-secretase activities may be involved in the processing of βAPP in order to generate β-Amyloid (Aβ) peptide, the aggregation and extracellular deposition of which in the brain is a hallmark of Alzheimer's disease pathology. Therefore, any therapeutic strategy evolved to prevent or halt the deposition of these plaques in Alzheimer's patients should take into account the activities of various β-secretases. A novel protease with enzymatic characteristics of β-secretase as disclosed herein provides yet another target for screening of compounds to identify potential drug candidates for the treatment or prevention of Alzheimer's disease and other neurodegenerative disorders.

I. Definitions

Before the present assays are described, it is to be understood that this invention is not limited to particular methodology described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention pertains. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, "β-amyloid precursor protein" (APP or βAPP) refers to a polypeptide that is encoded by a gene of the same name localized in humans on the long arm of chromosome 21 and that includes a β-amyloid protein region within its carboxyl region.

The term "β-amyloid protein" (Aβ) as used herein refers to all β-amyloid proteins including approximately 43 amino acid peptide which comprises residues 597–640 of the 695 amino acid isotype of APP. β-amyloid proteins of the invention include any protein containing about 40 to about 44 amino acids which preferably comprises residues 597–640 of the 695 amino acid isotype APP, $A\beta_{1\text{-}40}$ or $A\beta_{1\text{-}42}$ (Selkoe et al., supra). Within this disclosure the term β-amyloid protein is intended to include the two major Aβ variants referred to herein and the 55 amino acid segments including amino acids 640–695 of the 695 amino acids isotype of APP. After this disclosure others will, perhaps, discover other β-amyloid proteins and as such as intended to come within the scope of the present invention.

The term "APP secretase," "secretase" and "secretase activity" as used interchangeably herein refers to any proteolytic enzyme and/or activity which results in the secretion of various fragments or intracellular fragmentation and degradation of APP. This includes α-secretase, β-secretase, γ-secretase, and any similar but as of yet unidentified enzymes which cause the proteolysis of either APP or Aβ.

The term "β-secretase" and "β-secretase activity" as used interchangeably herein refers to the enzyme or enzymes responsible for proteolysis of APP at the N-terminal cleavage site of APP, which occurs between residues 596 and 597 and at residues 605 and 606 of the 695 isotype of APP.

The term "APP/β-secretase mixture" as used herein refers to the isolated APP and α-secretase as a complex and/or as a mixture of the two substances.

The term "Alzheimer's disease" (abbreviated herein as "AD") as used herein refers to a condition associated with formation of neuritic plaques comprising β-amyloid protein primarily in the hippocampus and cerebral cortex, as well as impairment in both learning and memory. "AD" as used herein is meant to encompass both AD as well as AD-type pathologies.

The term "AD-type pathology" as used herein refers to a combination of CNS alterations including, but not limited to, formation of neuritic plaques containing β-amyloid protein in the hippocampus and cerebral cortex. Such AD-type pathologies can include, but are not necessarily limited to, disorders associated with aberrant expression and/or deposition of APP, overexpression of APP, expression of aberrant APP gene products, and other phenomena associated with AD. Exemplary AD-type pathologies include, but are not necessarily limited to, AD-type pathologies associated with Down's syndrome that is associated with overexpression of APP.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

The term "cerebral amyloid angiopathy" (abbreviated herein as CAA) as used herein refers to a condition associated with formation of amyloid deposition within cerebral vessels which can be complicated by cerebral parenchymal hemorrhage. CAA is also associated with increased risk of stroke as well as development of cerebellar and subarachnoid hemorrhages (Vinters (1987) *Stroke* 18:311–324; Haan et al. (1994) *Dementia* 5:210–213; Itoh, et al. (1993) *J. Neurol. Sci.* 116:135–414). CAA can also be associated with dementia prior to onset of hemorrhages. The vascular amyloid deposits associated with CAA can exist in the absence of AD, but are more frequently associated with AD.

The term "phenomenon associated with cerebral amyloid angiopathy" as used herein refers to a molecular, structural, or functional event associated with CAA, particularly such an event that is readily assessable in an animal model. Such events include, but are not limited to, amyloid deposition, cerebral parenchymal hemorrhage, and other CAA-associated characteristics.

The term "β-amyloid deposit" as used herein refers to a deposit in the brain composed of Aβ as well as other substances.

By "antibody" is meant an immunoglobulin protein which is capable of binding an antigen. Antibody as used herein is meant to include the entire antibody as well as any antibody fragments (e.g., $F(Ab')_2$, Fab', Fab, Fv) capable of binding the epitope, antigen or antigenic fragment of interest.

Antibodies of the invention are immunoreactive or immunospecific for and therefore specifically and selectively bind specific proteolytic products of the APP protein. Antibodies for each proteolytic product are preferably immunospecific—i.e., not substantially cross-reactive with other proteolytic products of APP. Although the term "antibody" encompasses all types of antibodies both polyclonal and monoclonal antibodies, and produced using a peptide antigen.

By "purified antibody" is meant one which is sufficiently free of other proteins, carbohydrates, and lipids with which it is naturally associated. Such an antibody "preferentially binds" to a proteolytic APP protein product (or an antigenic fragment thereof), i.e., does not substantially recognize and bind to other antigenically-unrelated molecules. A purified antibody of the invention is preferably immunoreactive with and immunospecific for a particular APP protein product (e.g., pNTF) and more preferably will not react with other APP protein products.

By "antigenic fragment" of an APP proteolytic product is meant a portion of such a protein which is capable of binding an antibody used in the assay of the invention.

By "binds specifically" is meant high avidity and/or high affinity binding of an antibody to a specific polypeptide, i.e., epitope of a APP protein product. Antibody binding to its epitope on this specific polypeptide is preferably stronger than binding of the same antibody to any other epitope, particularly those which may be present in molecules in association with, or in the same sample, as the specific polypeptide of interest, e.g., binds more strongly to APP protein product than other epitopes so that by adjusting binding conditions the antibody binds almost exclusively to the APP protein product. Antibodies which bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the compound on polypeptide of interest, e.g., by use of appropriate controls. In general, antibodies of the invention bind to a particular APP protein product with a binding affinity of $10^7$ moles/liter or more, preferably $10^8$ mole/liters or more. In general, an antibody with a binding affinity of $10^6$ moles/liter or less is not useful in that it will not bind antigen at a detectable level using conventional methodology currently used.

By "detectably labeled antibody" or "detectably labeled anti-βNTF" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (*Antibodies: A Laboratory Manual* (1988) Cold Spring Harbor Laboratory Press, Cold Spring Harbor, N.Y.).

The term "compound" as used herein describes any molecule, e.g., protein, naturally occurring substances, synthesized protein or small molecule pharmaceutical, with the capability of affecting secretase activity. Such compounds may be used to treat the molecular and clinical phenomena associated with amyloid-associated disorders, and specifically AD, CAA and prion-medicated disorder.

By "effective dose" or "amount effective" is meant an administration of a compound sufficient to provide the desired physiological and/or psychological change. This will vary depending on the patient, the disease and the treatment. The dose may either be a therapeutic dose, in which case it should sufficiently alter levels of amyloid plaques in the subject to alleviate or ameliorate the symptoms of the disorder or condition, or a prophylactic dose, which should be sufficient to prevent accumulation of amyloid plaques to an undesirable level. The terms "treatment,". "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease from occurring in a subject which may be predisposed to the disease but has not yet been diagnosed as having it;

(b) inhibiting the disease, i.e., arresting its development; or (c) relieving the disease, i.e., causing regression of the disease.

The therapeutic agents that can be identified using the assay of the invention are particularly useful in the treatment of any disease associated with the deposition of β-amyloid, including AD, hereditary cerebral hemorrhage with amyloidosis, and prion-mediated disorders, and the like.

The terms "neutral" and "pH 6.5" β-secretase activity are used interchangeably and refer to a polypeptide of about 32–39 kDa as determined by radiation inactivation analysis of HEK293 cell membrane extracts and 20–26 kDa as determined by radiation inactivation analysis of human brain samples, having the ability to cleave βAPP, and having a pH optimum of about 6.5–7.0. Similarly, the terms "acidic" and "pH 4.5" β-secretase activity are used interchangeably and refer to a polypeptide of about 50–60 kDa as determined by radiation inactivation analysis of HEK293 cell membrane extracts or human brain samples, having the ability to cleave βAPP, and having a pH optimum of about 4.5–5.5.

The term "alter" and grammatical variants thereof, when used in connection with the assays of the present invention, include any and all modifications, such as inhibition or enhancement of β-secretase activity.

The term "preferentially inhibits", and grammatical variants thereof, are used to refer to a molecule that exhibits a higher inhibitory activity towards a particular ("preferred") β-secretase enzyme than towards another ("less preferred") β-secretase enzyme. The ratio of the "referred" and "less preferred" β-secretase inhibitory activities is preferably at least about 1.5, more preferably at least about 2.0, even more preferably at least about 2.5.

II. General Assay Methodology

The present invention provides an assay method for identifying modulators (enhancers or, preferably, inhibitors) of β-secretase enzymatic activity. The method is based on screening for modulators (enhancers or inhibitors) of a novel "neutral" β-secretase activity. The novel β-secretase, in isolated, immobilized or cell bound form, is contacted with a candidate compound, or a plurality of candidate compounds, and those candidates are selected that have the ability to alter, preferably inhibit, the biological activity of the new "neutral" β-secretase. While the effect of a candidate compound on β-secretase activity is preferably detected by monitoring its ability to alter (e.g. inhibit) β-secretase mediated cleavage of APP, any other read-out of β-secretase activity is equally suitable. Both cell based and cell-free assays are specifically within the scope of the invention. Candidate compounds which provide significant inhibition, usually at least about 25%, preferably at least about 50%, more preferably at least about 75%, most preferably at least about 90% inhibition, and often at least about 95% inhibition, are considered β-secretase inhibitors.

In a preferred embodiment, the present invention provides an assay methodology for determining compounds which can have an effect on (preferably reduce) APP proteolytic products using membrane-enzyme mixtures, as well as methods of preparation of the mixtures used in such assays. Such compounds can be used in the treatment of patients, particularly humans, with amyloid-associated disorders. The assay involves contacting APP/β-secretase as individual components or as a mixture or complex with a test compound and thereafter determining the level of APP proteolytic products, and particularly βNTF. If the compound reduces the level of APP proteolytic products, e.g., as compared with a previously known standard then the compound is a candidate for the treatment of patient's with amyloid-associated disorders. The APP and β-secretase which are contacted with the compound can be both isolated from cell membranes obtained from cells expressing both APP and β-secretase or can be isolated from cells expressing either APP or β-secretase and then combined together. Alternatively, APP and/or β-secretase may be partially or fully synthesized by traditional chemical synthesis and/or recombinant DNA technology. In a special embodiment, cells engineered to recombinantly express APP and/or one or more β-secretases can be used.

Before the membranes are used in the assays, background levels of APP proteolytic products may be removed. This step could be eliminated by precisely determining the level of APP proteolytic products in a known cell culture of cells expressing APP. Thereafter the known level can be adjusted for in the assay, i.e., increases or decreases relative to the known background level could be determined by subtracting away the known background level. In order to perform the assay in this manner, it would, of course, be necessary to obtain cell membranes from a statistically significant number of recombinant cells which express a known level of APP and thereafter determining the background level of APP proteolytic products present in the membranes of these cells.

In one aspect of the invention there is a disclosed method of identifying a compound characterized by its ability to alter β-secretase activity. The method comprises the steps of (1) contacting APP/β-secretase mixture isolated from membranes obtained from cells, from which background levels of APP proteolytic products have been removed, with a test compound; and (2) determining levels of APP proteolytic products following contact with the test compound, wherein the levels of APP proteolytic products are indicative of the effect of the compound on in vivo β-secretase activity.

An assay method for determining compounds that affect APP β-secretase activity is disclosed which comprises: (1) preparation of APP and β-secretase from cell membranes prepared from cells expressing APP and β-secretase; (2) treatment of the APP/β-secretase with a candidate compound in vitro; and (3) determining the effect of the compound on β-secretase activity by measuring the levels of APP proteolytic products. It is preferable to run the assay against a control, e.g., where no compound is added to the APP/β-secretase mixture and/or where any carrier added with the test compound is added to a culture to determine if a carrier alone affects APP proteolysis.

Compounds found to affect β-secretase activity, e.g., either inhibit or enhance secretase activity, can be further assayed in transgenic mice. Compounds which test positive in the assay of the invention can be used in the treatment of amyloid-associated disorders such as AD and CAA.

Also described is a method of reducing the level of β-amyloid plaque in the brain tissue of a mammalian host by administering a compound which inhibits β-secretase as identified in the assay described above. Prophylactic use of such compounds is also contemplated for individuals at risk for Alzheimer's disease such as the elderly and/or individuals carrying known mutations linked to this disorder. Individuals treated may not presently exhibit symptoms but have been subjected to head and neuronal trauma.

Membrane Preparation and Isolation of APP/β-Secretase Mixture

The membrane preparations of the invention are prepared to allow access of the endogenous or exogenous APP protein with β-secretase isolated from membrane preparations. Membrane preparations used in the assay of the invention can be homogenized using techniques available to those skilled in the art, such as douncing, use of a mechanical tissue homogenizer, needle shearing, and use of a ball-bearing tissue homogenizer. Generally, cells of interest, e.g., primary glial cells, mammalian cells expressing endogenous or exogenous human APP, human 293 cells, and the like are isolated and disrupted in a manner to preserve the β-secretase activity. The cells used for the membrane preparation may be freshly obtained, e.g., isolated from a patient sample, from a cultured system, e.g., an immortal cell line, or cells present in long-term storage, e.g., cells stored at −70° C. Once the membranes have been isolated, they may be used directly in the assay or stored at −70° C.

Once a crude cell membrane preparation has been generated, the membranes are treated with a mild detergent to remove background levels of APP β-secretase proteolytic products (βNTF). An exemplary detergent for use with the presently described assay include 0.02–0.05% saponin. Following treatment with the mild detergent, the P2 membrane is solubilized with a stronger detergent, such as 0.3% Titron X-100 or 0.3% Triton X-100 (reduced form).

Once solubilized, the APP/β-secretase mixture is partially purified. It can be purified using any method known in the art, but is preferably purified using chromatography, e.g., Q-HP Sepharose chromatography. Other techniques that may be used include, but are not limited to, anion exchange chromatographies such as DEAE and DMAE.

Optionally, before addition of a test compound, the APP/β-secretase mixture is exposed to an agent that alters β-secretase activity and/or stabilizes the detectable APP proteolytic products of β-secretase. In a preferred embodiment, the agent enhances the level of β-secretase activity in order to allow for improved detection of alterations in β-secretase activity. Exemplary agents for this use include phospholipids such as cardiolipin, L-α-phosphatidylserine and L-α-phosphatidylinositol. Other agents affecting β-secretase activity can be used in the present invention as well, as will be obvious to one skilled in the art upon reading this disclosure.

Detection of Proteolytic Products Following Treatment of APP/β-Secretase Mixture Following incubation of the APP/β-secretase mixture with the test compound, the preparation is assayed for levels of β-secretase proteolytic products of APP, e.g., βNTF. Detection of the APP β-secretase proteolytic products can be accomplished using any of a number of methods to determine the absence or presence or altered amounts of the differentially expressed polypeptide in the test sample. For example, detection can utilize staining of the APP/β-secretase mixture with labeled antibodies, performed in accordance with conventional methods. In general, antibodies that specifically bind a differentially expressed polypeptide of the invention are added to a sample, and incubated for a period of time sufficient to allow binding to the epitope, usually at least about 30 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g., fluorescein, rhodamine, Texas Red, etc.). The absence or presence of antibody binding can be determined by various methods, including flow cytometry of dissociated cells, microscopy, radiography, scintillation counting, etc. Any suitable alternative method of qualitative or quantitative detection of levels or amounts of differentially expressed polypeptide can be used, for example western blot, immunoprecipitation, radioimmunoassay, etc.

In a preferred embodiment, an enzyme-linked immunosorbent assay (ELISA) is used to detect the presence of the APP/β-secretase proteolytic product, βNTF. Quantitation of multiple samples can be made more time efficient by running the assay in an ELISA format in which different potential agents are tested against cell membrane preparations and rapid quantitation is accomplished by spectrophotometric or colorimetric detection. For example, the presence of a relatively low amount of βNTF indicates a decrease in β-secretase activity. Such changes in the level of APP proteolytic peptide products can identify lead compounds for further study in the treatment of amyloid-associated disorders.

III. Compounds of the Invention

Compounds of the invention encompass numerous chemical classes, including but not limited to the compounds described herein with known function. Novel methods are provided which employ compounds that are effective in altering β-secretase activity levels. Compounds found to inhibit or enhance β-secretase activity can be further assayed in transgenic mice to determine additional physiological effects and potential of the compound as a therapeutic agent (Moran et al. *Proc. Natl. Acad. Sci. USA* 92: 5341–5345 [1995]; Games et al. *Nature* 373: 523–527 [1995]; Haiso et al. *Science* 274: 99–102 [1996]). Compounds which test positive can be used in a specific method of treatment of the invention described below.

Candidate compounds can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs.

Compounds for use in the method of invention may be small organic compounds having a molecular weight of more than 50 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomoleculese including, but not limited to: peptides, saccharides, fatty acids, steroids, purines, pyrimidines, derivatives, structural analogs or combinations thereof.

IV. Methods of Treatment Using Compounds of the Invention

The method of treatment is a method of reducing the level of β-amyloid plaque in the brain tissue of a mammalian host by administering a compound which showed positive results in the assay described above. In general, such compounds will reduce the level of β-amyloid plaque in brain tissue by affecting in vivo levels of β-secretase. Therapeutic effects may be seen, for example, by compounds that inhibit or decrease β-secretase activity. Prophylactic use is also contemplated for individuals at risk for Alzheimer's disease such as the elderly and/or individuals carrying known mutations linked to this disorder. Individuals treated may not presently exhibit symptoms but have been subjected to head and neuronal trauma.

In the subject methods, the compound may be administered to the host using any convenient means capable of resulting in the desired target protein activity modulation. Thus, the compound can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, transdermal patches, suppositories, injections, inhalants and aerosols.

As such, administration of the compounds can be achieved in various ways, including oral, buccal, rectal, parenteral, intraperitoneal, intravaginal, intradermal, transdermal, intratracheal, etc., administration.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the compounds can be used alone or in combination with appropriate additives to make tablets, powders, granules or capsules. Examples of additives are conventional additives, such as lactose, mannitol, corn starch or potato starch; binders, such as crystalline cellulose, cellulose derivatives, acacia, corn starch or gelatins; disintegrators, such as corn starch, potato starch or sodium carboxymethylcellulose; lubricants, such as talc or magnesium stearate; and if desired, diluents, buffering agents, moistening agents, preservatives and flavoring agents.

The compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol. If desired, conventional additives such as solubilizers, isotonic agents, suspending agents, emulsifying agents, stabilizers and preservatives may also be added. The concentration of therapeutically active compound in the formulation may vary from about 0.5–100 wt. %.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit (e.g., a teaspoonful, tablespoonful, tablet or suppository) contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The compounds are administered to a host in a physiologically acceptable carrier, at a dosage from 5 mg to 1400 mg, more usually from 100 mg to 1000 mg, preferably 500 mg to 700 mg for a dose of 0.5 to 20 mg/kg weight. The dosage for compounds altering secretase activity is elected so that the secretase activity is altered by 10 to 80%, more preferably 20 to 70% and even more preferably 25–50%.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Membrane Preparation Protocol

Membrane preparations for APP/β-secretase substrate mixtures were generated from human embryonic kidney 293 cells (HEK293) expressing the 751 form of APP carrying the "Swedish" AD mutation (293/751sw). For other purposes such as following or purifying β-secretase activity, membrane extracts were made from naïve HEK293 cells. This protocol can also be used for all other cell types, e.g. Chinese hamster ovary cells expressing an exogenous human APP gene (CHO-695APP). Cells were stored as cell pellets at −80° C. until used for the preparation.

Approximately 70–100 gram of cells (wet weight) were routinely used to generate 50–100 mls of enzyme substrate complex/mixture from membrane extracts. The cells were thawed and were resuspended through different iterations in a total volume of 12–15×vol/gram wet weight of TE/1× protease inhibitor cocktail (PIC) buffer [20 mM Tris-HCl/5 mM EDTA pH 8.5 (TE) with 1×PIC (1×PIC: 10 μM leupeptin, 1 μM aprotinin and 1 μM pepstatin, Boehringer Mannheim). Initially, the pellet was resuspended in ~6–9× vol/gram wet weight and homogenized using a tissumizer (IKA Labortechnik, Staufen, Germany) at medium setting for three times one minute with intermittent cooling on ice. The homogenate was then distributed into different 50 ml Falcon tubes and was centrifuged for 10 minutes at 1500 rpm in a table centrifuge (Sorvall) at 4° C. After the centrifugation, the supernatant corresponding to a PNS (postnuclear supernatant) was carefully removed and pooled into a fresh tube. In order to avoid disturbing the relatively loose pellet, approximately 10 ml of material were left in each tube including the pellet that contained unbroken cells and nuclei. The pellet and remaining supernatant was pooled and resuspended in the remainder of the homogenization buffer. The suspension was then subjected to another round of homogenization with the tissumizer followed by centrifugation and supernatant collection as described above. The resulting PNS was pooled with the previously saved material. If deemed necessary, an additional round of homogenization was included or the previously centrifuged material was spun again to recover all the supernatant efficiently. The membranes were then recovered by centrifugation of the pooled PNS at 28,000 rpm (~65,000×g) in a Ti45 rotor (Beckman, Palo Alto, Calif.) for 30–40 min at 4° C. and the supernatant was poured off carefully after the centrifugation.

Example 2

Detergent Wash of Membrane Preparation

Membrane preparations as prepared in Example 1 are treated with a mild detergent to reduce, preferably to undetectable levels, background APP proteolytic products. The membrane pellet was resuspended sequentially in a total of 12×vol/gram wet weight of TE/1×PIC in the presence of a final concentration of 0.02% saponin (added from a 0.5% saponin stock solution made in distilled water). The pellet was homogenized on ice by 13–18 strokes in a Kontes glass tissue homogenizer with a tight pestle (0.013–0.14 mm clearance). Treatment with the mild detergent saponin permeabilizes the membranes and thus releases lumenal soluble proteins. In particular, this preferably reduces, to undetectable levels, any background APP proteolytic products, such as β-NTF. Following homogenization of the membranes on ice, the suspension was centrifuged in a Ti45 rotor at 28,000 rpm (~65,000×g) for 30–40 minutes. The saponin extract containing β-NTF was stored at −80° C. until it was further purified over a Q-HP column (similarly to the membrane extract described below) and the resulting fractions containing β-NTF were aliquoted and stored at −80° C. for use as a standard. The pellet after the saponin extraction was resuspended again in TE/1×PIC, 0.02% saponin and treated as described, and this step was repeated until the membranes were washed in a total of 12×vol/gram cell paste.

Following the saponin extraction, the final membrane pellet (P2 pellet) was routinely frozen at −80° C. until further use. When needed, the frozen P2 pellet was thawed and resuspended in TE/1×PIC. Triton X100—R was added to a final concentration of 0.3% and the suspension was dounced on ice at least 12 times in a Kontes glass tissue homogenizer with a tight pestle (0.013–0.14 mm clearance). After the material had been suspended well, the solution was centrifuged at 32,000 rpm (~100,000×g) for 45–60 minutes at 4° C. The solubilized membrane supernatant was collected, and the pellet discarded. The solubilized Triton X100 extract was then filtered through a 0.45 μm bottle-top filter to remove insoluble material (Schleicher & Schüll) and was partially purified on a 25 ml Q-HP Sepharose column (Pharmacia, Stamford, Conn.) in the following manner.

Example 3

Partial Purification of the APP/β-Secretase Mixture

The detergent-treated membrane preparations of Example 2 are partially purified using a Q-HP Sepharose chromatography column (Pharmacia, Stamford, Conn.). The Q-HP column was equilibrated with 5–10 column volumes (CVs) of equilibration buffer [20 mM Tris/EDTA pH 8.5, 0.05% Triton X100—R] and the extract was loaded at 5 ml/minutes. The column was then washed with 5 CVs of equilibration buffer to remove non-specifically bound proteins. Proteins including APP and β-secretase were eluted from the column with a linear gradient from 0–1M NaCl in equilibration buffer [TE, 0.05% Triton X100-R] over 5 CVs and ~8 ml fractions were collected. 1×PIC was added to the collection tubes prior to the run.

Following elution, the column was washed well with 1M NaCl/TE buffer, and 0.5N NaOH with intermittent rinses in distilled water and was then re-equilibrated and stored at 4° C. until future use. For long-term usage, the column was further washed with 20% ethanol/water and stored therein.

The total protein concentration for each sample was determined using a BCA protein test (Pierce, Rockford, Ill.), and a protein profile was also determined for the rinses and the elution. Alternatively, protein was followed with a UV monitor. Samples were run on an SDS-polyacrylamide gel for Western Blot analysis, and blotted with pAb369, an antibody which recognizes the C-terminus of APP (Gouras et al. *Proc. Natl. Acad. Sci. USA* 97: 1202–1205 [2000]). The saponin extract of washes was also blotted to analyze the βNTF using AF-20 series antibodies or equivalent. βNTF-specific antibodies were generated against the neoepitope produced by β-secretase cleavage of APP. Specifically a peptide to the neoepitope ([C]ISEVNL) based on the Swedish APP sequence was synthesized, conjugated to a protein carrier via the N-terminal cysteine on the peptide, and used to immunize rabbits according to standard procedures. The resulting antiserum was affinity purified using the peptide immunogen.

Individual fractions were then assayed for the presence of APP using an ELISA as well as for the presence of β-secretase using the native substrate assay as described in Examples 4 and 6. Fractions containing APP and β-secretase as determined by Western blotting (see above) or by ELISA (Examples 4 and 6) were pooled as APP/β-secretase complex/mixture, aliquoted and stored at −80° C. for future use.

Example 4

ELISA Assay Using Partially Purified APP/β-Secretase Mixture

The β-secretase ELISA assays were performed as per the scheme in FIG. 1. Each well of a 96 well plate containing a flat bottom (high protein binding, Corning, N.Y.) was coated with 100 μl of the monoclonal capture antibody 8E5 (at ~8–10 μg/ml) (Johnson-Wood et al. *Proc. Natl. Acad. Sci. USA* 94: 1550–1555 [1997]). The plate was then covered with parafilm and incubated overnight at 4° C. or alternatively for 2 hours at 37° C. Following incubation, any excess liquid was removed, wells blotted dry and incubated with 150 μl of blocking buffer (0.1% BSA/PBS) per well at 37° C. or room temperature for 1–2 hours.

The partially purified APP/β-Secretase complex solution (10 μl or 20 μl) was placed either in 1.5 ml microfuge tube or 96-well assay plate, and covered well with the cap or parafilm respectively. A solution containing the compound of interest was added to the APP/β-secretase mixture, followed by the addition of assay buffer [50 mM potassium phosphate, 5 mM EDTA, 0.02% Triton X-100, pH 6.5] to a final volume of 100 μl. Cardiolipin can be added to improve the signal (see Example 5) and the assay can tolerate up to 2% DMSO when testing compounds solubilized in DMSO. While this example describes the standard reaction conditions at pH 6.5, the assay was also routinely performed at a different pH, in particular at pH 7.0 or pH 4.5. The reaction samples were incubated at 37° C. for 6–18 hours and were then stopped by placing the samples at −20° C. This reaction can be carried out for multiple potential compounds simultaneously to provide a high throughput method of screening multiple candidate therapeutic agents.

Figure 2:
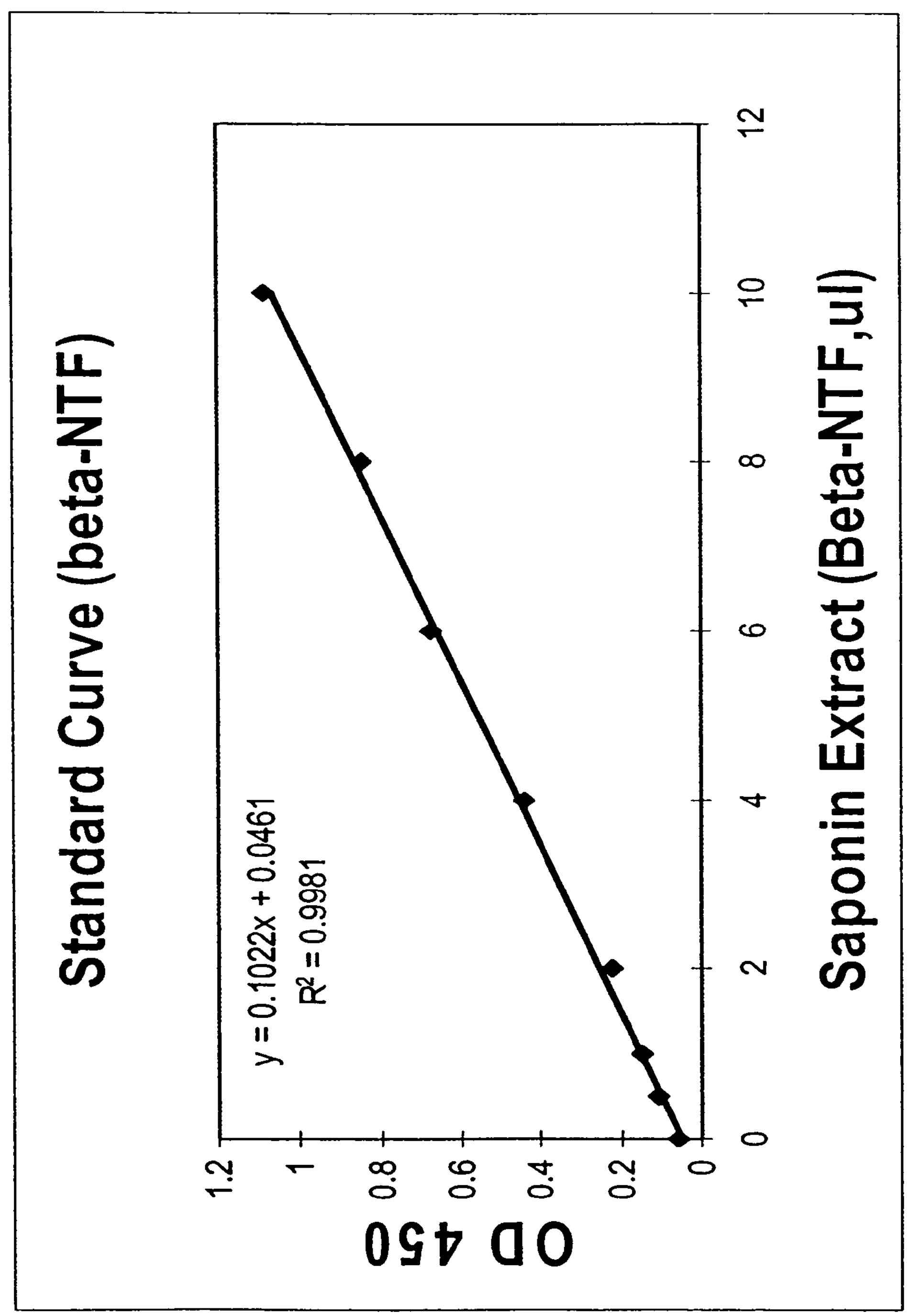
FIG. 2 is a graph showing linear response of endogenous β-secretase cleavage product, βNTF, in the assay.
Figure 3:
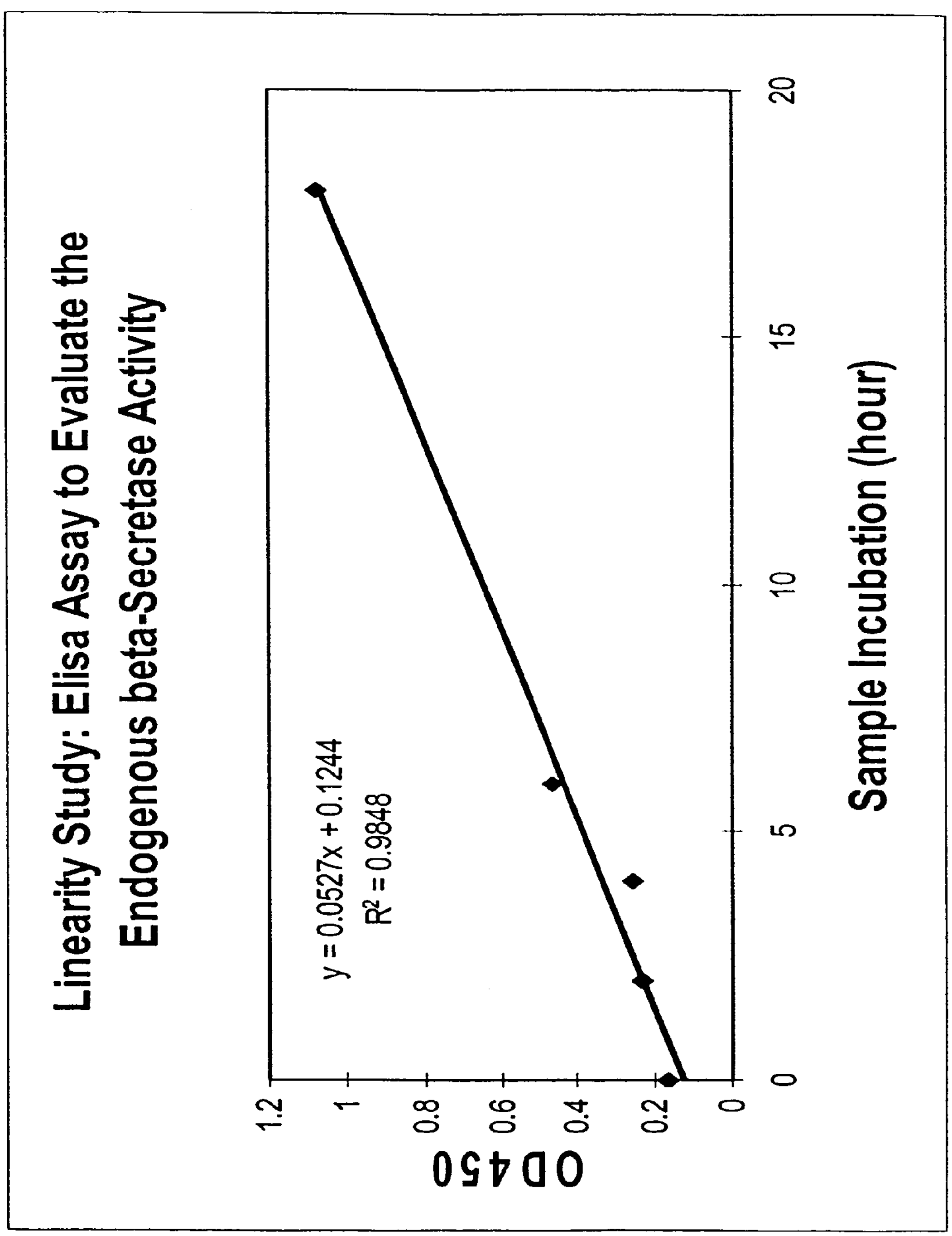
FIG. 3 shows endogenous β-secretase activity as a function of incubation time.

After removing blocking buffer, the coated plates were blot dried. To one set of wells, different volumes (e.g. 0, 0.5, 1, 2, 4, 8, and 10 μl) of the Saponin wash from the membrane preparation were added. These were diluted to a final volume of 100 μl with dilution buffer and served to establish the linearity of the assay (typically in the OD 450 nm range from 0.06 to 1.2) (FIG. 2). The measurement of β-NTF was found to vary linearly with the amount of incubation time in the assay (FIG. 3).

To another set of remaining wells, 50 μl of a β-secretase reaction performed in the presence of a particular compound or combination of compounds was added, followed by the addition of dilution buffer (50 μl) to make up the volume to 100 μl/well. The ELISA plate was incubated at room temperature for 1–2 hours. Following incubation, the plate was washed three times with 200 μl of Wash Buffer (50 mM Tris-HCl pH 7.5, 150 mM NaCl, 0.05% Tween-20), and blot dried. Alternatively, PBS, 0.05% Tween-20 can be used as wash buffer. One hundred μl of 1:5000 dilution of the affinity purified anti-β-NTF AF-#20 antibodies in Antibody/Conjugate Buffer [PBS, 2% BSA, 0.05% Tween-20] was then added to each well and the plate incubated at room temperature for 1 hour. The plate was again washed three times with wash buffer, and excess liquid was removed between washes.

One hundred μl of a 1:5000 dilution of a goat anti rabbit IgG-HRP in Antibody-Conjugate Buffer was then added to each well, and the plate incubated at room temperature for one hour. After the secondary antibody incubation, the plate was washed three times with wash buffer. One hundred μl of TMB/$H_2O_2$ (Sigma) that had been brought to room temperature during the previous incubation was then added to each well. During the development of 5–20 minutes, the plate was covered with aluminum foil and stored in the dark. After sufficient blue color had developed, the reactions were stopped by adding 100 μl of 5N $H_2SO_4$ to each well, and the amount of βNTF was determined by reading the plate at 450 mm in a Softmax spectrophotometer.

Example 5

Inhibition of β-Secretase Activity by AEBSF

The ability of the broad spectrum, irreversible serine protease inhibitor AEBSF to inhibit β-secretase activity was tested using the methods of the invention. AEBSF has been implicated as an inhibitor of β-secretase activity (M. Citron et al., *Neuron* 17:171–179 (1996)), and so was a promising candidate to test using the method of the invention.

Twenty μl of the APP/β-secretase mixture produced using the method described in Examples 1–3 was diluted 1:4 in 80 μl assay buffer [50 mM potassium phosphate, 5 mM EDTA, 0.02% Triton X-100, at pH 7.0]. Cardiolipin was assessed in the assay over a concentration range from 0.01–100 μM. To assess the effects of an inhibitor, AEBSF (Pefabloc) was added at concentrations varying from 0 mM to 10 mM. The samples were incubated at 37° C. for 16 hours, and the level of β-secretase activity was determined using the ELISA assay of Example 4.

Figure 4A:
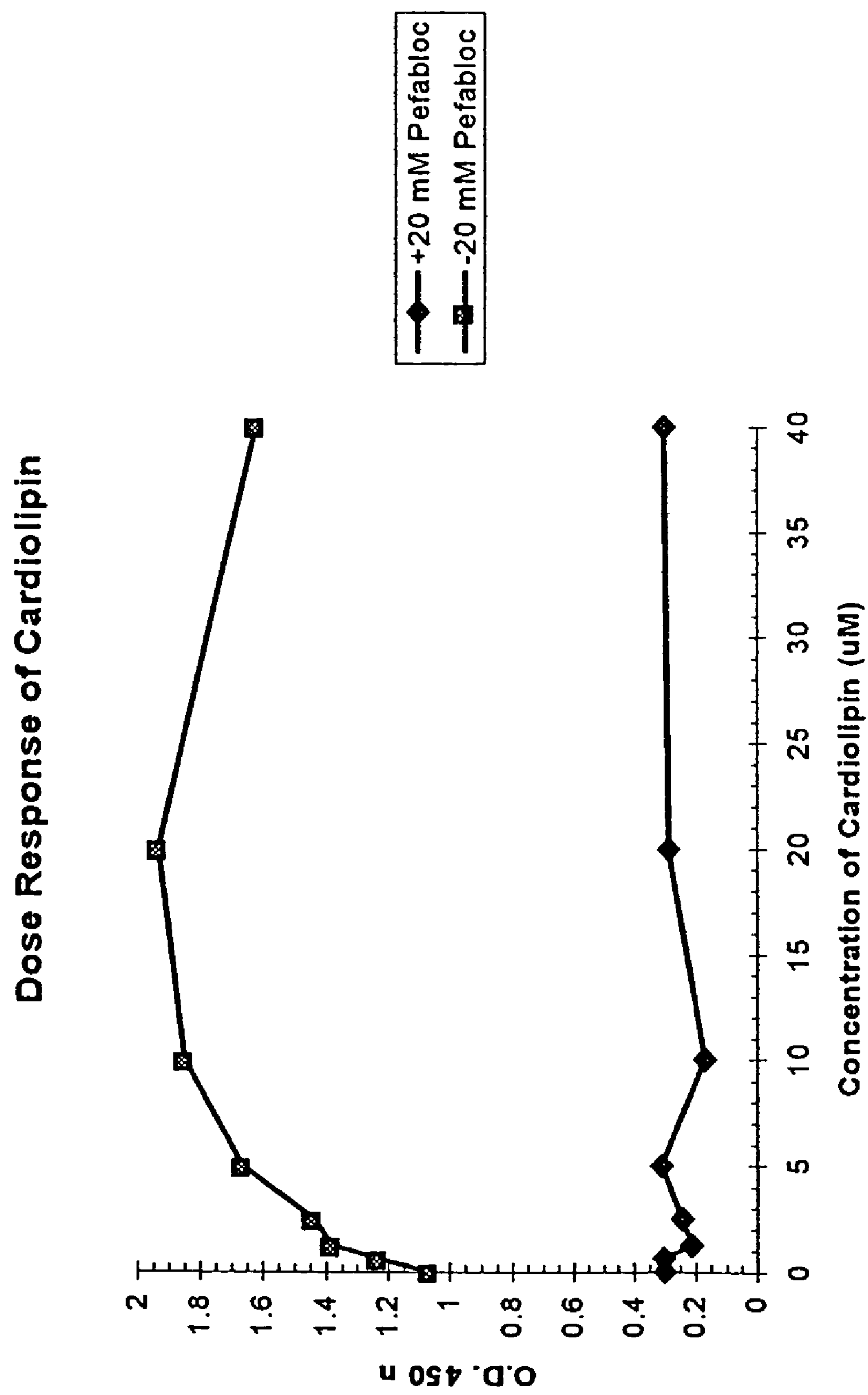
Figure 4B:
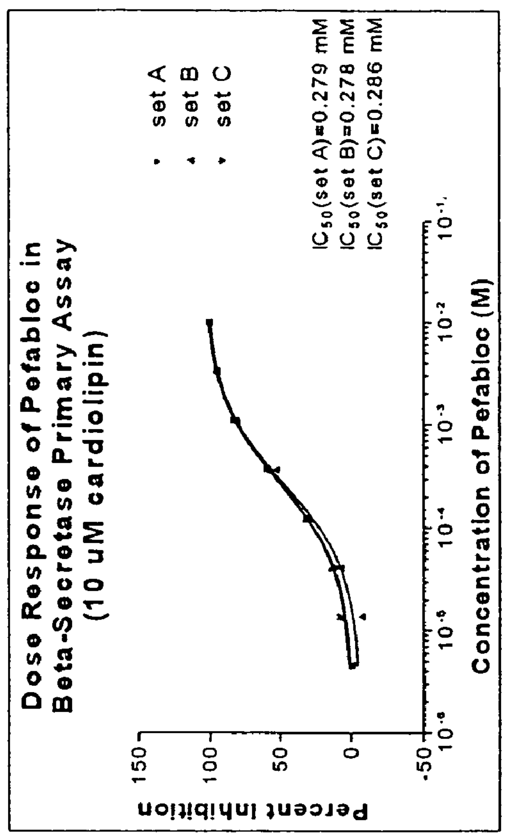
FIG. 4B shows the percentage inhibition of β-secretase activity.
Figure 4B:
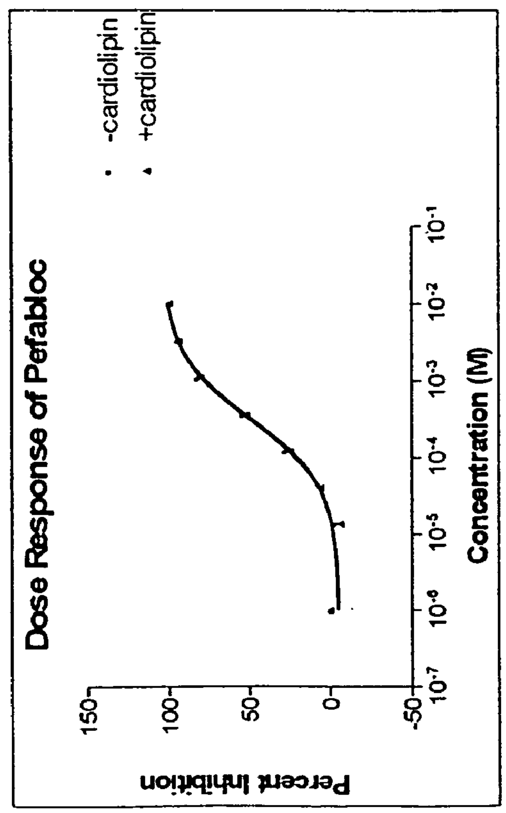

The presence of cardiolipin in the assay buffer provided a dose-dependent increase in the detectable levels of β-secretase activity (FIG. 4A). The AEBSF (Pefabloc) exhibited dose-dependent β-secretase inhibition using standard assay conditions (FIG. 4B). These results show that 1) the assay of the invention allows for detectable decrease in β-secretase activity upon exposure to a known inhibitor, and 2) the detectable decrease is more dramatic with the addition of a compound such as cardiolipin that increases β-secretase activity. This is particularly useful in the detection of compounds that have more subtle effects on the activity of β-secretase.

The potent, irreversible, membrane permeant active site serine hydrolase inhibitor, diisopropyl fluorophosphate (DFP) did not inhibit the activity of the neutral β-secretase activity. Indeed, at high concentrations of the inhibitor, β-NTF production was enhanced by pre-treatment of the extracted enzyme with DFP. The inhibitory effect of modification of an activated serine residue is either directly or indirectly involved in the catalytic mechanism of β-NTF production by the neutral β-secretase.

Example 6

β-Secretase Activity and APP Assay

The fractions obtained during the purification of β-secretase and/or APP substrate as described in Example 3 were assayed in the following manner. The assay consists of two different parts, an incubation or reaction phase to generate β-NTF and an ELISA part to capture and measure the β-NTF generated by β-secretase. The ELISA was carried out essentially as described in Example 4.

After the column had been run, the reaction plate was set up to measure β-secretase activity in the following manner using a 96 well plate with a conical bottom (Corning, N.Y.). Of each fraction, 10 or 20 μl was added to 90 or 80 μl of assay buffer (50 mM potassium phosphate, pH 6.5, 5 mM EDTA, 0.02% Triton X100-R, 10 μM cardiolipin) so that the total reaction volume was 100 μl. While this example describes the standard reaction conditions at pH 6.5, the assay was also routinely performed at a different pH, in particular at pH 4.5 (see below). In the case of naïve HEK293 cells that were not transfected with APP751sw or if β-secretase was followed in fractions devoid of substrate, exogenous APP751sw (prepared as described in Example 7) was also added to the reactions. Half of the reaction was then transferred to a new 96 well plate. Both plates were tightly sealed using an Aluminium plate seal (Beckman) to avoid excess evaporation of the reaction mix. One of the plates was then placed overnight at −20° C. for the control reaction during which time the other plate was incubated in a 37° C. incubator.

In the meantime, the corresponding plates for the ELISA assay were set up as described earlier in Example 4. The next morning, after the reaction plates had been incubated for 15–18 hours, the 37° C. plate was placed at −20° C. to stop the reaction. The ELISA plate that had been coated overnight was then blotted dry and incubated with 150 μl of blocking buffer (0.1% BSA/PBS) per well at 37° C. or room temperature for 1–2 hours. When the ELISA plates were blocked, the reaction plates were removed from −20° C. and thawed for the actual ELISA. The blocking solution was removed from the ELISA plate and the plate was blotted dry and then washed once with Wash Buffer (PBS, 0.05% Tween-20). Excess wash buffer was removed and the plate blotted dry. Different volumes of Saponin wash were used to establish a linear response curve for PNTF as described in Example 4. For the reactions, 30 μl from each well of the reaction plates incubated either at −20° C. or 37° C., respectively, were added to the ELISA wells. Reaction samples were diluted with 70 μl of dilution buffer [PBS, 0.02% Triton X100-R, 0.3%–6% BSA] and then incubated at room temperature for 60–80 minutes. After this incubation, excess liquid was discarded and the wells were washed 3–4 times with wash buffer. The rest of the steps in the ELISA were carried out as described in Example 4 to determine the amount of βNTF generated as a result of β-secretase activity.

To determine the substrate (APP) levels in these fractions, either 10 μl of the −20° C. reaction mix or 10 μl from the fractions directly were added onto ELISA wells coated with the 8E5 antibody and blocked as described above. The samples were diluted with 90 μl dilution buffer and the ELISA was performed basically as described above except that the detection system was slightly different. APP was detected using a primary biotinylated monoclonal 2H3 antibody at a dilution of 1:2000 (Johnson-Wood et al. *Proc. Natl. Acad. Sci. USA* 94: 1550–1555 [1997]), followed by a streptavidin-HRP conjugate (Zymed) used at 1:5000.

Example 7

Figure 5:
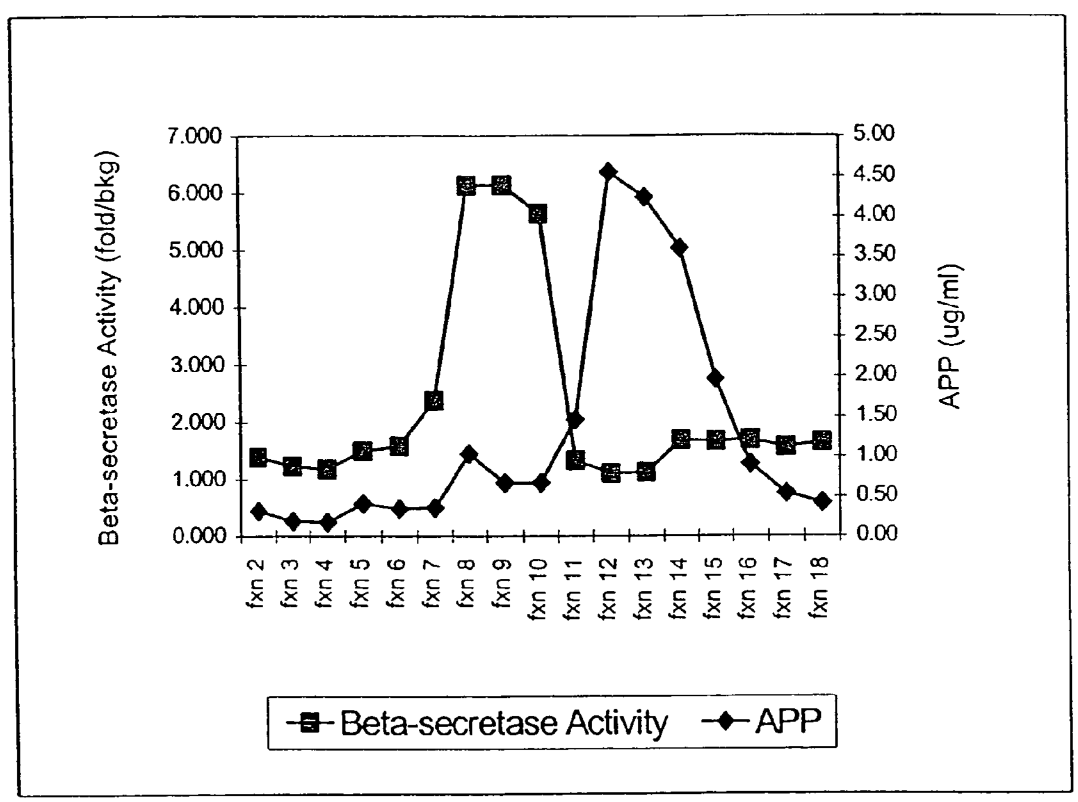
FIG. 5 shows chromatographic separation of the APP751sw substrate and the endogenous β-secretase activity on Mono Q column.

Generation of Partially Purified APP751SW Substrate for the Measurement of β-Secretase Activity in the Absence of Endogenous Substrate In the previous example, we described the generation of β-secretase/APP enzyme substrate complex. In order to be able to follow and purify β-secretase from cells such as naïve HEK293 or CHO cells or from brain extracts, we need to reconstitute the activity by adding back exogenous APP substrate to individual samples such as fractions from a column purification step. We thus developed a partial purification approach that allowed us to obtain APP751sw substrate devoid of endogenous β-secretase activity as measured at pH 6.5. APP751sw was expressed and purified from transiently transfected HEK293T cells. Transient transfection of APP751sw improved the separation since a significantly higher ratio of substrate to enzyme could be obtained. Cells were transiently transfected in roller bottles by a transfection method recommended by the manufacturer using FuGene 6 (Boehringer Mannheim). The cells were harvested and the equivalent of ~5–10 gms of cell paste was subjected to detergent extraction using the protocol described in Examples 1, 2, and 3 with the corresponding buffer volumes. The detergent extract was separated on a 1 ml Q-HP Sepharose column, and as observed when preparing APP/β-secretase complex as described in Examples 1, 2, and 3, both β-secretase and APP751 sw were initially found to co-fractionate on this column. The APP751sw containing fractions were then pooled and the pool was diluted ~8–10 fold with equilibration buffer [20 mM Tris/EDTA pH 8.5, 0.05% Triton X100-R] to reduce the salt from the previous chromatography step. The material was then loaded onto a Mono Q column that had been equilibrated. Non-specifically bound proteins were washed with 10 CVs of equilibration buffer and proteins were eluted with a 15 CV linear gradient from 0–1 M NaCl in equilibration buffer. Again, fractions were analyzed for the presence of APP751sw as described in Example 6. The β-secretase activity was determined at pH 6.5 and the protocol was very similar to what is described in Example 6 except that additional, exogenous APP751sw substrate from a previous preparation was added to each of the reactions. This was necessary since otherwise β-secretase would not have been detectable in fractions that were very limited in APP751sw substrate (FIG. 5). As shown in FIG. 5, the mono Q step allowed the separation of the APP751sw substrate from the bulk of the endogenous β-secretase as measured at pH 6.5. Based on this procedure, we have routinely obtained APP751sw at concentrations of ~4–6 μg/ml and use ~3–8 μl per reaction to determine the β-secretase activity when substrate needs to be added back to the reaction mixture. The β-secretase activity devoid of substrate from this column (compare FIG. 5) was also pooled for additional experiments (see Example 9).

Example 8

Identification and Separation of Two β-Secretase Activities that Operate at Different pH We investigated the pH profile of the β-Secretase activity in the native substrate assay in two ways. In these experiments, we first measured the pH profile of the APP/β-secretase complex that was prepared as described in Examples 1, 2, and 3. Second, we evaluated the pH profile of β-secretase that had been further separated from the APP751sw substrate on mono Q when added back and thus reconstituted with its substrate (see Example 7).

Figure 6A:
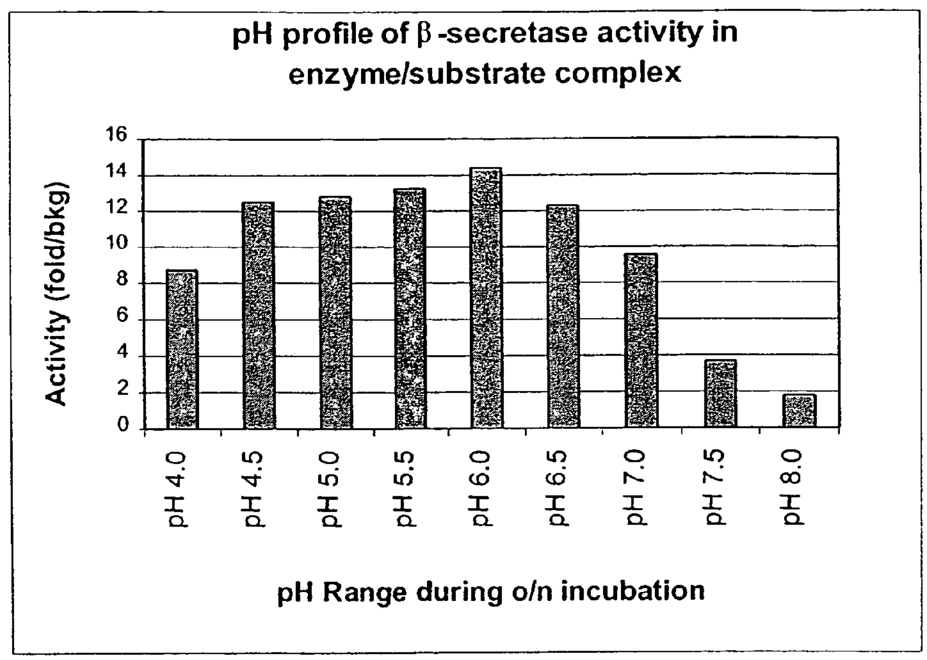
FIG. 6 shows pH profile of β-secretase activity in enzyme/substrate complex (A) or in partially purified fraction obtained from mono Q column and reconstituted with APP (B).

In the first experiment, the enzyme/substrate complex was incubated overnight as described above under different pH conditions (phosphate buffer, containing 10 μM cardiolipin and 0.02% Triton X100-R) ranging from pH 4.0 to pH 8.0. After the incubation, all samples were neutralized and then bound to the ELISA plate and β-NTF was determined as described above. As shown in FIG. 6A, the enzyme/substrate complex had a pH optimum of pH 6.0 to pH 6.5 under these conditions. This profile was relatively broad and significant activity was detected down to pH 4.5 and even as low as pH 4.0. These results suggested a rather heterogenous mixture of potentially more than one β-secretase activity.

Figure 6B:
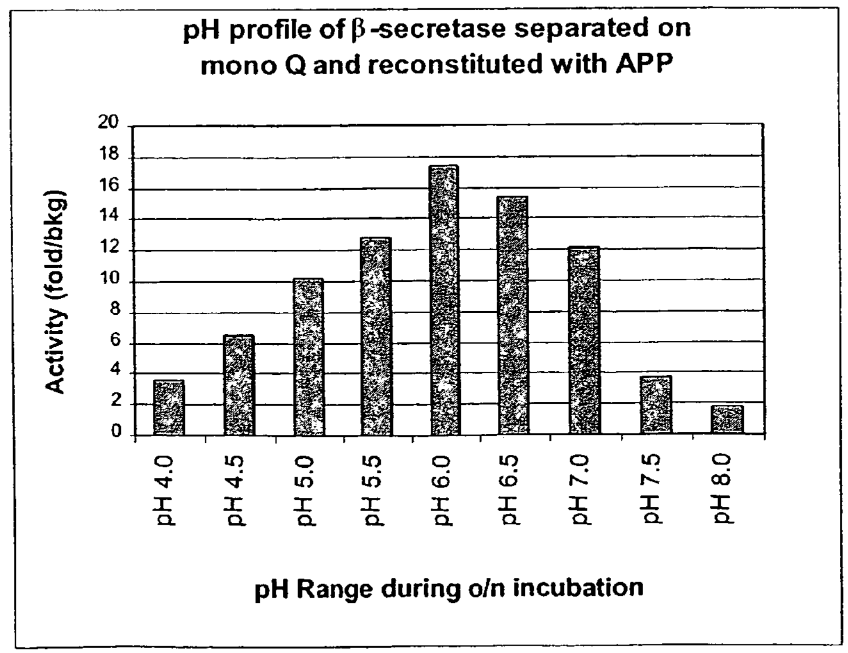

When we reconstituted the β-secretase pool that had been separated via the additional mono Q step with exogenous APP751sw substrate (compare Example 7), we saw a more pronounced activity optimum at pH 6.0/pH 6.5 (FIG. 6B). This suggested that the more neutral activity had been separated further on the mono Q column from the lower pH activity that was more significant in the starting material (FIG. 6A).

Taken together, these results clearly suggest the presence of two distinct β-secretase activities in HEK293 membranes, one that operates preferentially at a more neutral pH (pH 6.0–6.5) and another that seems to favor a more acidic pH.

Figure 7:
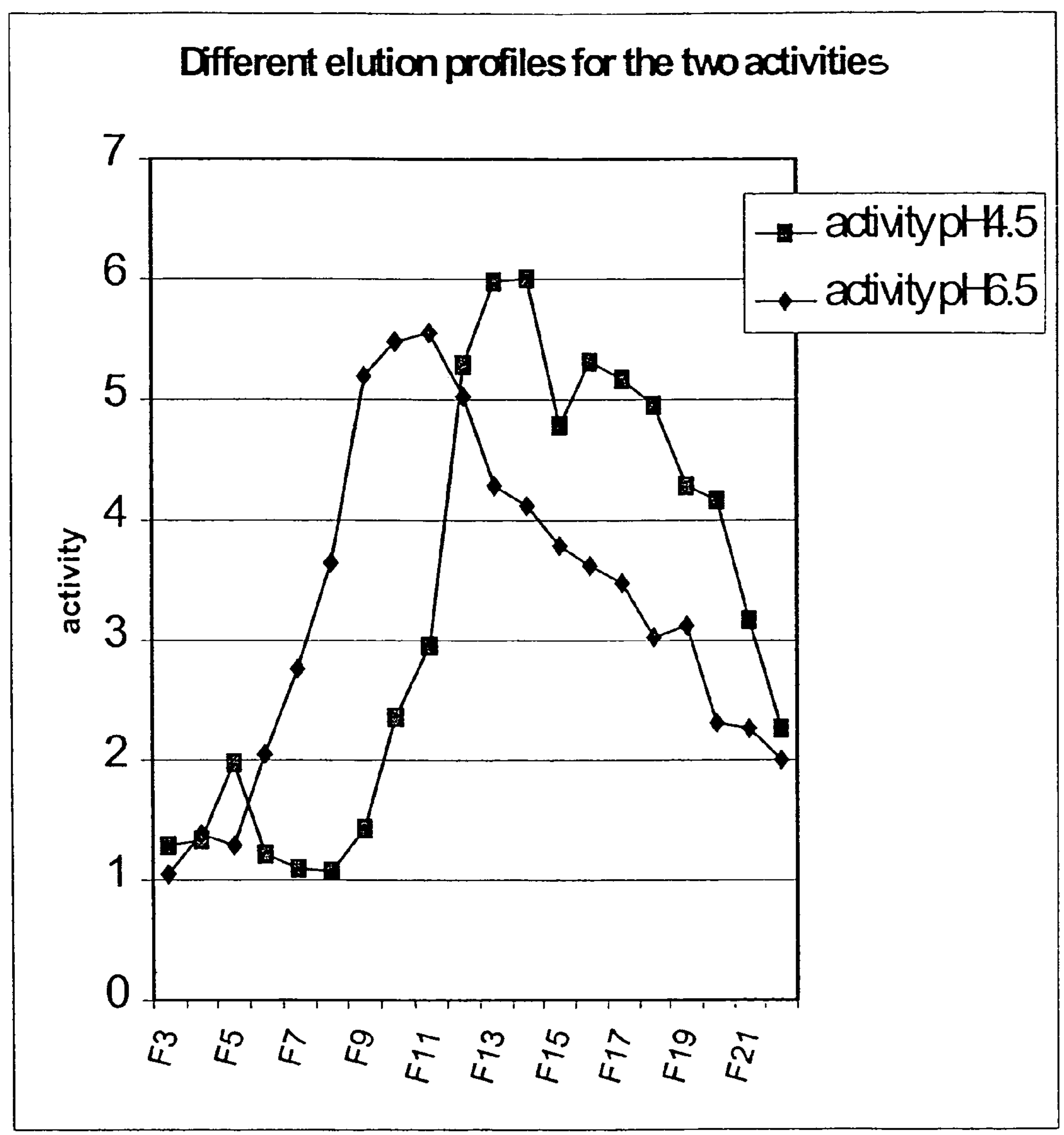
FIG. 7 shows elution profiles of β-secretase activities measured at pH 4.5 and 6.5.

In order to clarify the existence of these two distinct activities, we separated them by anion-exchange chromatography. Naïve HEK293 cells were homogenized and extracted as described in Examples 1, 2, and 3 except at a smaller scale. 30 gms of HEK293 cell paste was processed and the volumes of homogenization, washes and extractions were adjusted accordingly. The detergent extract was then loaded onto a 5 ml Q-HP Sepharose column and non-specifically bound proteins were washed with 10 CVs of equilibration buffer. Proteins were eluted from the column using a shallower gradient as that described in Example 3 to improve the separation between the two activities. Proteins were eluted in 12 CVs of a 0–1M NaCl gradient in equilibration buffer and the resulting fractions were measured for β-secretase activity using the native substrate assay at both pH 4.5 and pH 6.5 (in phosphate buffer as described above). These cells did not contain any endogenous APP751 sw substrate and thus each reaction was supplemented with substrate (obtained as described in Example 7). As shown in FIG. 7, two distinct elution profiles were clearly visible. The activity operating preferentially at pH 4.5 was thus distinct and could be separated from that active at pH 6.5. We thus have provided evidence that there are two distinct β-secretase entities with differential pH profiles.

Example 9

Two Separate Activities Contribute to β-Secretase Activity in Membrane Extracts

Figure 8:
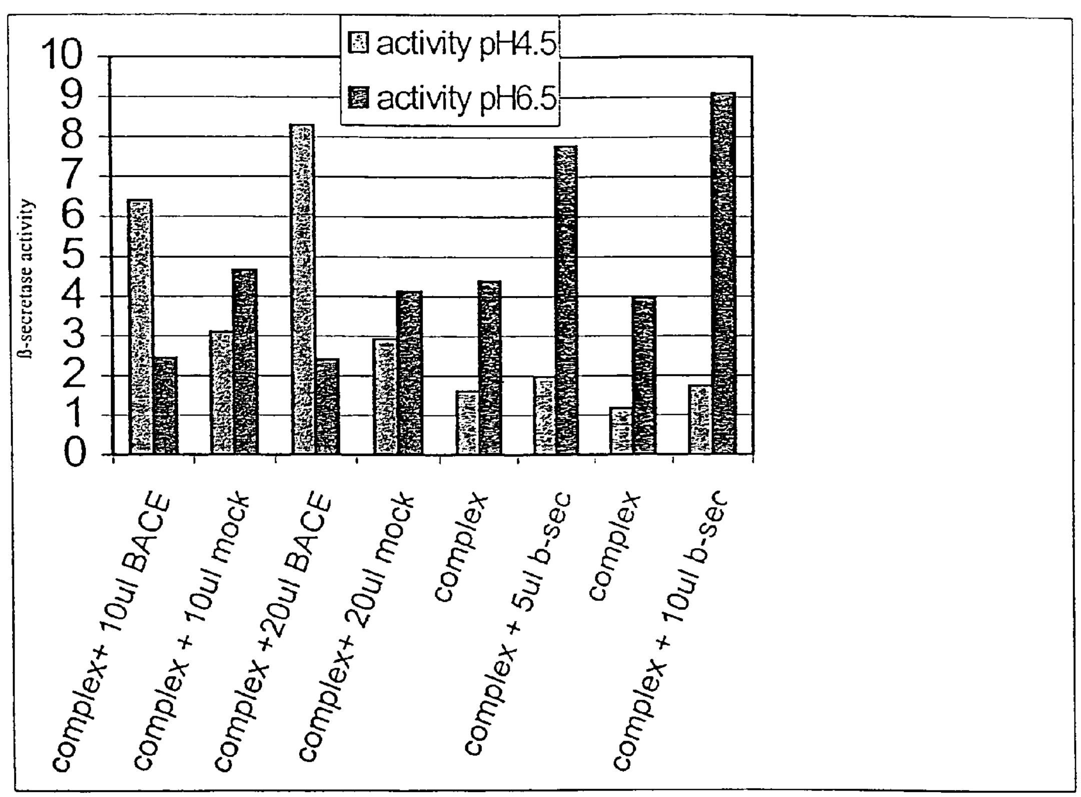
FIG. 8 shows the effect of the addition of purified recombinant BACE or partially purified β-secretase (as described in Example 7) on β-secretase activity present in APP/β-secretase complex (as described in Example 6) monitored at pH 4.5 and pH 6.5.

BACE Fc fusion protein was expressed in HEK293EBNA cells and purified basically as described (Vassar et al., *Science* 285:735 [1999]). Cell supernatants from BACE transfected or mock-treated cells were purified on Protein A Sepharose and eluates were first diluted with PBS and then concentrated ~10 fold in a Millipore micro-concentrator. 5 to 10 μl of BACE fusion protein, mock eluate or partially purified β-secretase (from Example 7) were added to 10 μl of enzyme/substrate complex (prepared as described in Examples 1, 2, and 3) and β-secretase activity was measured at either pH 4.5 or pH 6.5. Two effects became apparent in this experiment. First, addition of different amounts of BACE (as opposed to mock-purified material) clearly enhanced the β-secretase activity measured at pH 4.5 but not at pH 6.5 (FIG. 8). Thus, BACE did not contribute significantly to the pH 6.5 activity that appeared to be more prominent in the complex preparations (compare complex alone at both pHs). Second, addition of partially purified neutral β-secretase activity from the mono Q column (compare Example 7), clearly enhanced β-secretase activity at pH 6.5 as expected but not at pH 4.5 (FIG. 8). Thus, these data underline that the neutral activity is different from BACE.

In conclusion, these data are consistent with the above results (Example 8) and provide independent evidence about the existence of distinct β-secretase activities in HEK293 cells. One activity preferentially acts at low pH and most likely represents BACE or a BACE-related protein while the other activity appears distinct from BACE and operates at a more physiological pH.

Example 10

Differential Effect of StatVal Inhibitor on Low Versus Neutral pH Activity

We used the statine substrate analog inhibitor (statVal) that targets BACE (Sinha et al., *Nature* 402, 537–540, 1999) to determine its effect on the different β-secretase activities described in Example 8. Two different samples were analyzed in the presence of the statVal inhibitor in the native substrate assay (Example 6–9). First, the enzyme/substrate complex that contained APP751sv and second, the different pH pools separated from naïve HEK293 cells that lacked the APP751sw substrate (Example 8). The assay was performed in both pH 4.5 and pH 6.5 reaction buffers and in the case of the pH pools, exogenous APP751sw substrate was supplemented in the reactions (Examples 6–9).

Figure 9A:
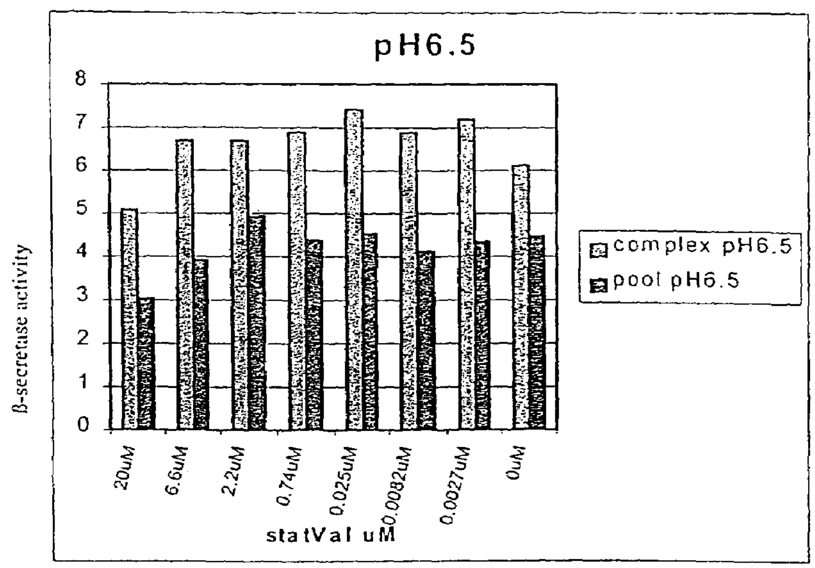
FIG. 9 shows the effect of StatVal inhibitor on β-secretase activity monitored at pH 6.5 (A) or pH 4.5 (B).
Figure 9B:
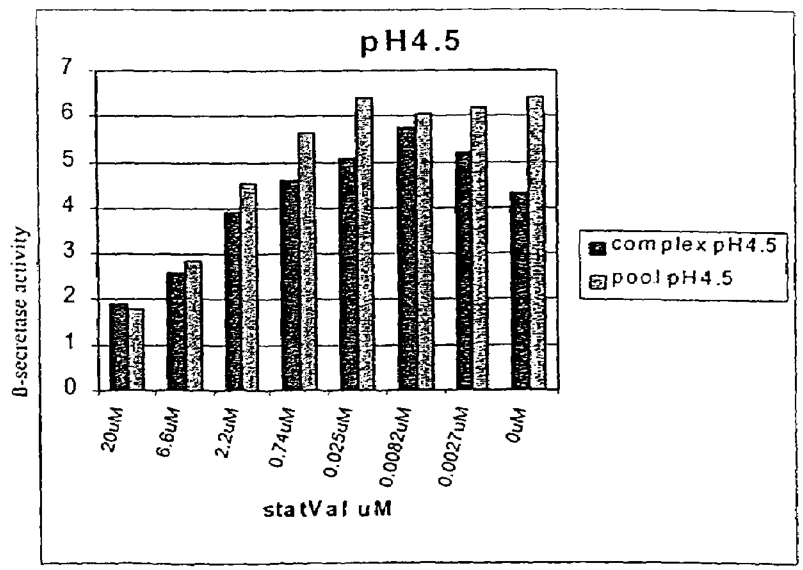
Figure 10:
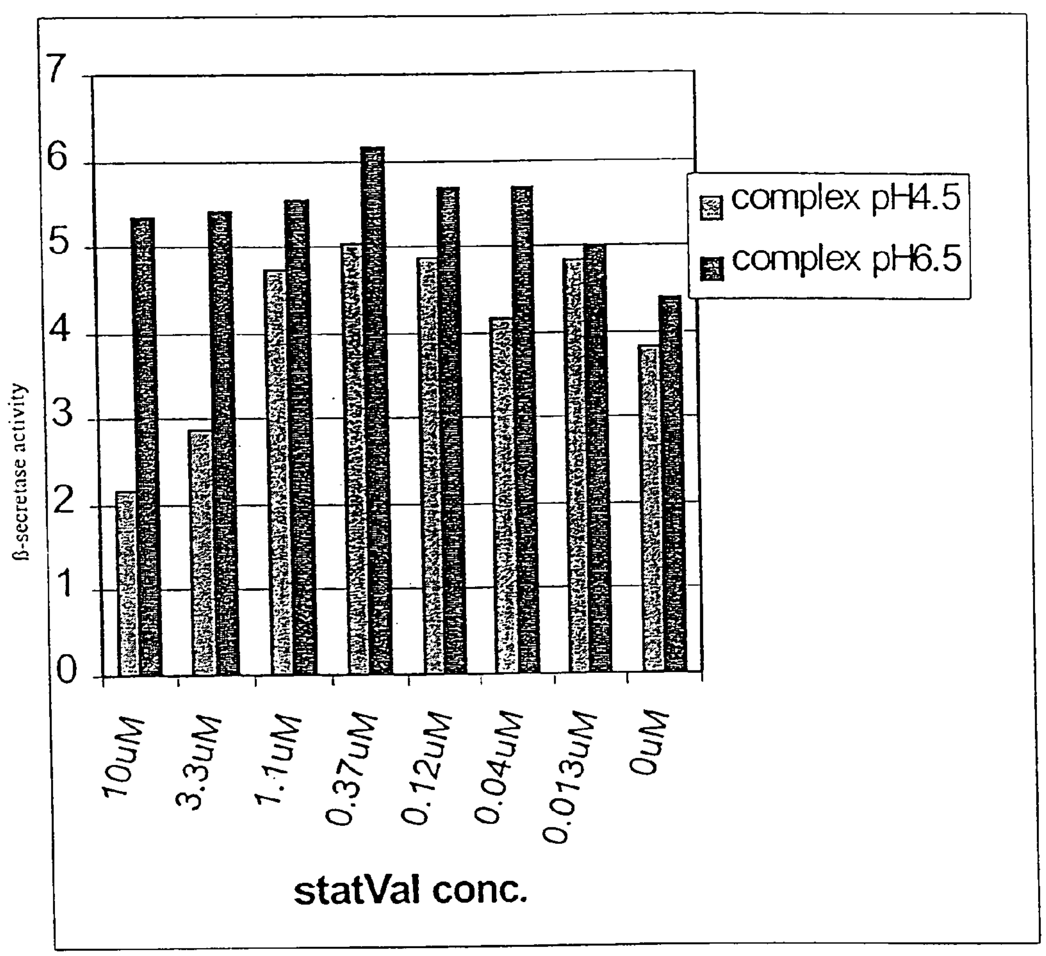
FIG. 10 shows the effect of StatVal inhibitor on β-secretase activity at pH 4.5 and pH 6.5.

The statVal inhibitor was added from a 10× stock at a final concentration of 20 μM to 0 μM using threefold serial dilutions. Given the good solubility of the peptide inhibitor, all serial dilutions generating the different 10× stocks were done in potassium phosphate reaction buffer, pH 6.5, in the absence of cardiolipin. The reactions and the ELISA were performed as described. FIGS. 9A and B show response curves from statVal inhibition experiments performed in either pH 6.5 or pH 4.5 reaction buffers, respectively. Both the enzyme/substrate complex (complex) as well as the reconstituted reaction (pH 4.5 pool) showed a pronounced parallel inhibition profile in the pH 4.5 reaction with an IC50 of ≦6.6 μM (FIG. 9B). In contrast, the pH 6.5 reaction was not significantly affected in either enzyme/substrate complex or the reconstituted reaction (FIG. 9A). Only at 20 μM, did we see some moderate effects but the IC50 for inhibiting the neutral activity was clearly ≧20 μM. FIG. 10 shows the same effect on enzyme/substrate complex treated with the statine inhibitor between 10 μM and 0 μM in either pH 4.5 or pH 6.5 reaction buffer (complex pH 4.5 versus complex pH 6.5). Again, as seen in FIG. 9, the statVal inhibitor discriminated against the two activities that had been detected and separated as described in Example 8.

Thus, we provided additional evidence that these different β-secretase activities are indeed distinct entities. They are separable according to their elution behavior from Q-HP Sepharose (Example 8) and they apparently show differential inhibition by the statVal inhibitor that was shown to target and bind BACE (Sinha et al., *Nature* 402, 537–540, 1999). Thus, the pH 6.5 or neutral β-secretase activity can be distinguished from BACE by two different criteria.

Example 11

Determination of Molecular Weight of β-Secretase with pH Optima at 4.5 or 6.5

It is possible to determine the molecular weight of a protein mediating a specific biological function using radiation inactivation (Kemper *Anal. Biochem.* 276: 113 [1999]; Kemper *Trends in Biochem. Sci.* 18: 236 [1993]). With radiation target analysis, biologically active samples are exposed at low temperature to high energy electrons. This ionizing radiation causes gross structural damage in the macromolecule and function is destroyed. The larger the mass of the protein, the more likely it will be destroyed. Determination of surviving activity after increasing radiation exposure permits estimates of the mass of the protein structure needed for the measured function since the rate of change is directly dependent on the mass. Only the primary molecular weight, not the secondary modifications, of a protein responsible for an activity is measured by radiation inactivation. This calculated estimate is independent of other protein molecules, hence, the protein of interest need not be pure: size estimates have been routinely made in intact cells, tissues or crude samples.

The molecular weight of the protein responsible for the activity at neutral pH present in the HEK293 human kidney fibroblasts membrane complex was estimated. HEK293 membranes were aliquoted into individual vials, frozen to −130° C., and the aliquots were subject to 12 different radiation doses, ranging from approximately 1 to 140 Mrad. High energy 10 MeV electrons were generated by a linear accelerator. After irradiation, the 12 vials containing the frozen irradiated HEK-293 membranes (6 mg/ml protein) were opened and purged with compressed nitrogen. Membranes were thawed at room temperature and centrifuged at 14,000 rpm in a microcentrifuge for 25 minutes at 4° C. Triton X-100 membrane protein extractions were made basically as outlined in Example 1–3. Supernatants were aspirated and the membrane pellets were resuspended and rehomogenized in Extraction Buffer (0.3% Triton X-100 (reduced), 20 mM Tris, 5 mM EDTA, pH 8.5). Samples were shaken for 2 hours at 4° C., followed by another 14,000 rpm centrifugation for 25 minutes at 4° C. Supernatants (protein extracts) were removed and assayed for protein concentration. Sample extracts were stored at −80° C. The sample extracts were thawed and diluted in Extraction Buffer to the desired stock protein concentration. These were then further diluted 1 to 20 in Complete Assay Buffer (0.02% Triton X-100 (reduced), 305 mM $K_2HPO_4$, 195 mM $KH_2PO_4$, 5 mM EDTA, pH 7.0, 10 μM cardiolipin (Avanti Polar Lipids). Forty μl was added to each well of a 96-well microplate (Costar). Twenty μl of partially purified swAPP substrate, diluted to 1.05 μg swAPP/ml in Complete Assay Buffer, was then added to the corresponding wells and the reaction was allowed to proceed in a humidified incubator at 37° C. for 24 hours. The reactions were assayed for level of β-NTF produced using the β-NTF ELISA as described in Examples 4 and 6.

Figure 11:
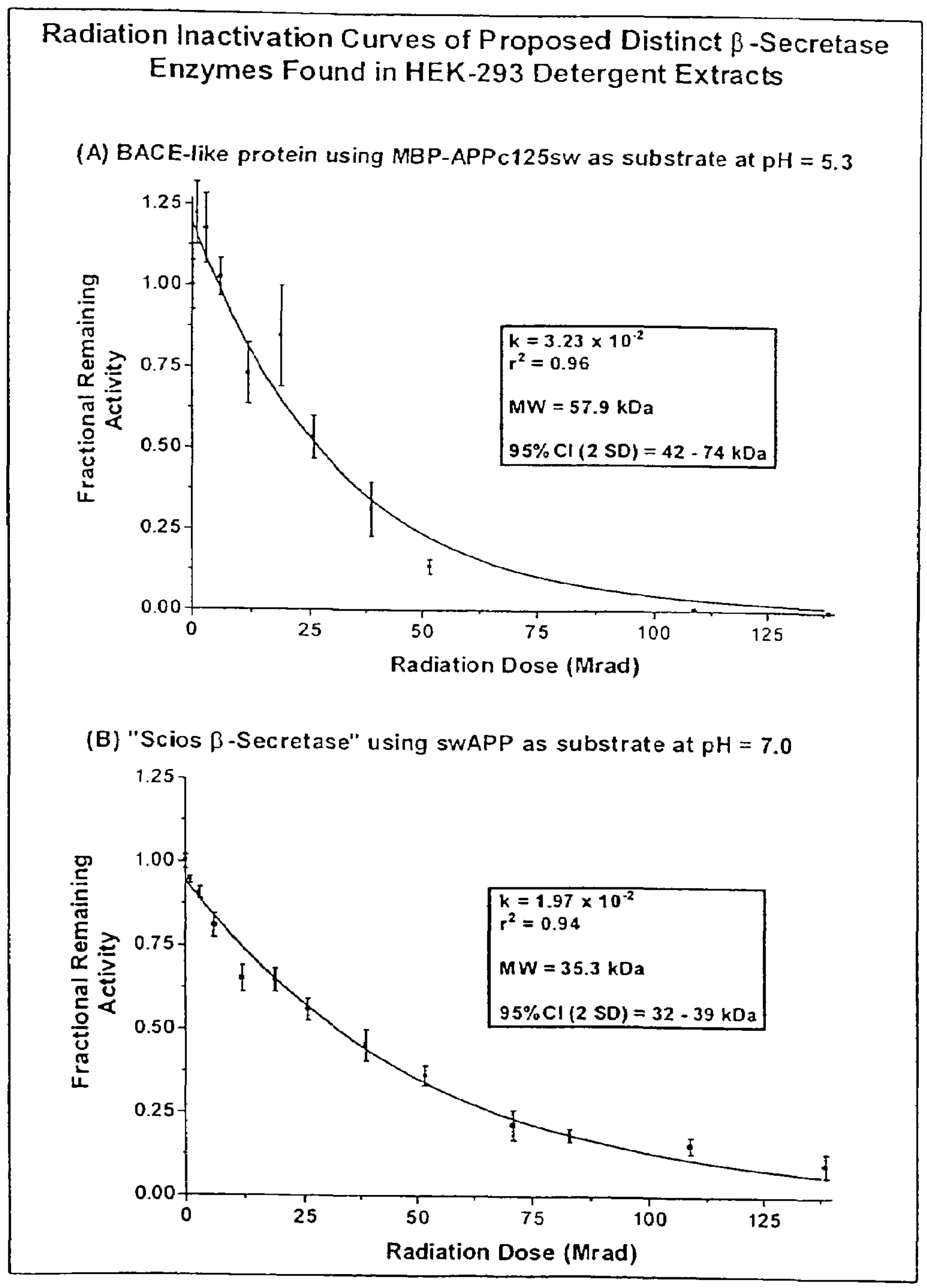
FIG. 11 shows determination of molecular weight of a protein responsible for β-secretase activity at pH 4.0 (A) and at pH 7.0 (B) in HEK293 cell membrane extract by radiation inactivation analysis.

The activity based on β-NTF production remaining after irradiation of the frozen HEK293 membrane pellets was analyzed by target theory, yielding the molecular weight of the functional unit i.e., neutral pH activity. The probability of particle collision with the target is described by the Poisson distribution: $P(n)=(e^{-x}x^{n})n!^{-1}$ where n is the number of primary ionizations per molecule when x is the average number of collisions (hits). Since the only biological activity which remains after radiation is from molecules which have not been hit, i.e. for which n=0, $P(0)=(e^{-x}x^{0})0!^{-1}=e^{-x}$. The average number of hits is therefore given by x=KD, where D is the radiation dose in rads (1 rad=100 ergs energy absorbed/gm matter). K is a constant related to the mass of the peptide and also containing conversion factors to change units from ergs per gram to hits per dalton. The biological activity, i.e., level of β-NTF generation, surviving after sample irradiation is expressed as a fraction of the activity in non radiated control samples. Since each hit in a biochemically active unit destroys that unit completely, the probability of no hits (obtained from the Poisson distribution) will also be the probability of surviving activity. Therefore, if a number of frozen samples are irradiated with varying doses, the fractional surviving activity is therefore $A/A_0=e^{-}$ kD. the temperature at which the samples were irradiated, −130° C., Mr=1.792×1012k. Based on this calculation the estimated molecular weight of the protein responsible for the neutral pH activity in the HEK293 cell membrane complex is approximately 35.3 kDa. Radiation inactivation curves for the HEK293 membrane complex are shown in FIG. 11 Panel B. The calculated molecular weight of the neutral pH active protein is significantly different from the predicted size of mature BACE, 51 kDa, devoid of secondary post-translational modifications (Vassar et al. *Science* 285: 735 [1999])

Repeated experiments produced similar values for the functional molecular weight of the neutral pH activity. Internal controls in these studies were proteins of known molecular weight including yeast glucose-6-phosphate dehydrogenase (MW=102,000; target size=91,000) and alkaline phosphatase (MW=57,337; target size=57,495). Each control sample yielded the predicted molecular weight.

To further demonstrate the molecular weight difference between mature BACE and the neutral pH active protein, irradiation inactivation experiments were performed under conditions which should identify BACE. HEK293 cell membrane extracts were prepared and irradiated as described above. The surviving activity present in the samples was assayed at pH 5.3 using the method of Sinha et al. (*Nature* 402: 537 [1999]) which employs a semi-synthetic substrate. This semi-synthetic substrate is a chimeric protein comprised of the maltose binding protein linked to the C-terminal 125 amino acids of βAPP (MBP-APPc125sw). The generation of the β-NTF equivalent product was measured in the treated versus control samples using an ELISA identical to that described by Sinha et al (ibid). Based on irradiation inactivation calculations, the molecular weight of the pH5.3 activity was calculated to be 57.9 kDa which is consistent with the molecular weight of BACE determined by amino acid sequence. These data are shown in FIG. 11 Panel A.

Figure 12:
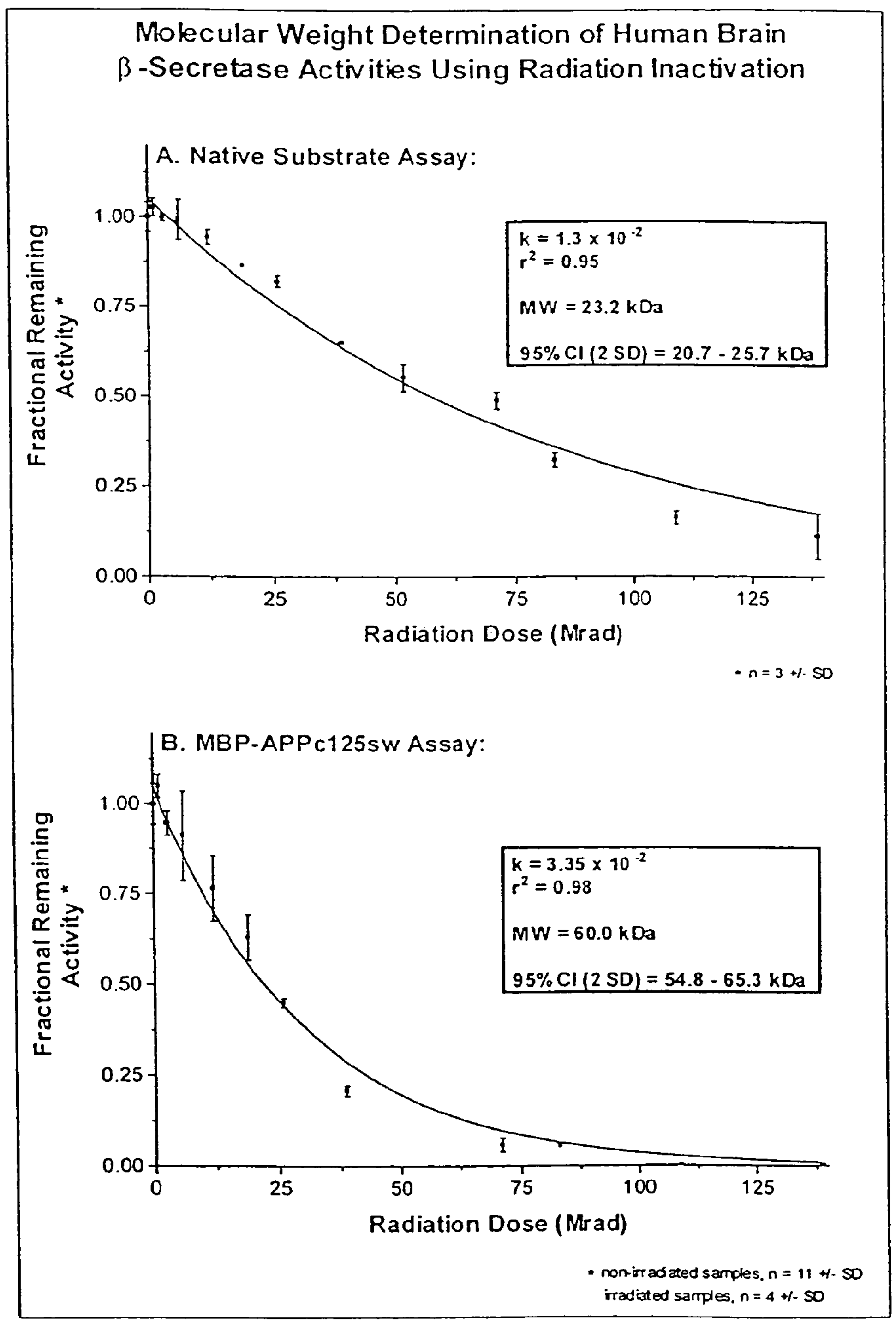
FIG. 12 shows determination of molecular weight of a protein responsible for β-secretase activity at pH 7.0 (A) and at pH 4.0 (B) in human brain extract by radiation inactivation analysis.

The functional target size was determined in human brain samples using identical methodology. The neutral pH target size was found to be approximately 23.2 kDa as shown in FIG. 12 Panel A. The target size for samples assayed under conditions for BACE (pH 5.3 using the semi-synthetic substrate MBP-APPc125sw) resulted in a molecular weight of 60.0 kDa as shown in FIG. 12 Panel B. From the human brain analysis, it is apparent that the neutral pH activity has a different molecular weight from BACE and is substantially unique.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. An isolated β-secretase enzyme obtainable from HEK293 cells or human brain, having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples.

2. An APP/β-secretase mixture comprising an isolated APP and an isolated β-secretase enzyme originating from HEK293 cells or human brain, having a pH optimum at about pH 6.5–7.0, and an estimated molecular weight of about 32–39 kDa as calculated from radiation inactivation analysis of HEK293 cell membrane extracts, or about 20–26 kDa as calculated from radiation inactivation analysis of human brain samples.

* * * * *